United States Patent
Dejima

(10) Patent No.: US 10,448,810 B2
(45) Date of Patent: Oct. 22, 2019

(54) SURGICAL APPARATUS FOR ENDOSCOPE AND OUTER TUBE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 305 days.

(21) Appl. No.: 15/470,914

(22) Filed: Mar. 28, 2017

(65) Prior Publication Data

US 2017/0196438 A1 Jul. 13, 2017

Related U.S. Application Data

(63) Continuation of application No. PCT/JP2015/077587, filed on Sep. 29, 2015.

(60) Provisional application No. 62/057,537, filed on Sep. 30, 2014.

(51) Int. Cl.
| | |
|---|---|
| *A61B 1/00* | (2006.01) |
| *A61B 17/34* | (2006.01) |
| *A61B 1/018* | (2006.01) |
| *A61B 1/313* | (2006.01) |

(52) U.S. Cl.
CPC ...... *A61B 1/00135* (2013.01); *A61B 1/00128* (2013.01); *A61B 1/00133* (2013.01); *A61B 1/00154* (2013.01); *A61B 1/018* (2013.01); *A61B 1/3132* (2013.01); *A61B 17/34* (2013.01); *A61B 17/3415* (2013.01)

(58) Field of Classification Search
None
See application file for complete search history.

(56) References Cited

U.S. PATENT DOCUMENTS

| | | | | |
|---|---|---|---|---|
| 2003/0135091 A1* | 7/2003 | Nakazawa | ......... | A61B 1/00073 600/113 |
| 2005/0119525 A1* | 6/2005 | Takemoto | .......... | A61B 1/00154 600/114 |
| 2015/0080650 A1 | 3/2015 | Dejima et al. | | |

FOREIGN PATENT DOCUMENTS

| | | |
|---|---|---|
| JP | S5986022 | 5/1984 |
| WO | 2013176167 | 11/2013 |

OTHER PUBLICATIONS

"Office Action of European Counterpart Application," dated Jan. 3, 2018, p. 1-p. 5, in which the listed reference as cited.
"International Search Report (Form PCT/ISA/210) of PCT/JP2015/077587", dated Dec. 22, 2015, with English translation thereof, pp. 1-2.

(Continued)

*Primary Examiner* — Aaron B Fairchild
(74) *Attorney, Agent, or Firm* — JCIPRNET

(57) ABSTRACT

Provided are a surgical apparatus for an endoscope and an outer tube that ease limitation of the types of available medical instruments to improve convenience and improve operability. An outer tube, which passes through a body wall, is inserted into a body cavity, and guides an endoscope and a treatment tool into the body cavity, includes therein a slider that is an interlocking member that moves the endoscope and the treatment tool forward and backward in an interlocking manner. The slider is provided with a cylindrical pressure-contact member that is brought into pressure-contact with and coupled to an outer peripheral surface of the treatment tool. The pressure-contact member is formed of compressible foamed rubber having pores, and an oil component is held in the pores of the foamed rubber.

10 Claims, 18 Drawing Sheets

(56) References Cited

OTHER PUBLICATIONS

"Written Opinion of the International Searching Authority of PCT/JP2015/077587", dated Dec. 22, 2015, with English translation thereof, pp. 1-6.
"Search Report of European Counterpart Application," dated Aug. 22, 2017, p. 1-p. 5.

* cited by examiner

SURGICAL APPARATUS FOR ENDOSCOPE AND OUTER TUBE

CROSS-REFERENCE TO RELATED APPLICATIONS

This application is a Continuation of PCT International Application No. PCT/JP2015/077587 filed on Sep. 29, 2015, which claims priority under 35 U.S.C. § 119(a) to U.S. Provisional Application No. 62/057,537 filed on Sep. 30, 2014. Each of the above applications is hereby expressly incorporated by reference, in their entirety, into the present application.

BACKGROUND OF THE INVENTION

1. Field of the Invention

The present invention relates to a surgical apparatus for an endoscope and an outer tube, and particularly, relates to a surgical apparatus for an endoscope and an outer tube that can operate an endoscope and a treatment tool inserted through two insertion passages provided in an outer tube in an interlocking manner.

2. Description of the Related Art

In recent years, since invasion to a patient is small compared to surgery in which a laparotomy, a thoracotomy, or the like, is performed, endoscopic surgery using endoscopes (hard endoscopes), such as a laparoscope, is widely performed. In the endoscopic surgery, a plurality of holes are made in a patient's body wall, an endoscope is inserted into a body cavity from one hole of them, and a treatment tool is inserted into the body cavity from another hole. Then, treatment of a living body tissue is performed with the treatment tool while observing the living body tissue within the body cavity with the endoscope.

Generally, in the endoscopic surgery, one or a plurality of treatment tools are used simultaneously with the endoscope. Therefore, since it is difficult for one operator to simultaneously operate the endoscope and the plurality of treatment tools, for example, a task where the operator operates treatment tools using both hands while making an assistant called an endoscopic technician operate the endoscope is normally performed.

In this way, in the endoscopic surgery, it is general that the operator's hands are bound by the operation of the treatment tool, and the operation of the endoscope is performed by the assistant. Therefore, in a case where the observation position of the endoscope is changed, the operator should serially give instructions to the assistant. Hence, the task of correctly directing the orientation of the endoscope to a direction desired by the operator is difficult, and stress is likely to be imposed on the operator. Additionally, since the assistant performs an operation after the operator issues an instruction, there is a tendency that surgery time is likely to be prolonged. Additionally, the assistant should operate the endoscope so as not to interfere with an operator's procedure, and the operation is likely to become complicated.

In contrast, the applicant of the present application suggests a technique in which an endoscope and a treatment tool are combined together by an outer tube, and if the treatment tool is moved forward and backward, the endoscope is also moved forward and backward in an interlocking manner with this movement of the treatment tool (refer to WO2013/176167A). Specifically, the outer tube that guides an insertion part of the endoscope and an insertion part of the treatment tool into a body cavity includes a tubular outer tube body that is inserted in a state where the insertion part of the endoscope and the insertion part of the treatment tool are made to be parallel to each other. An interlocking member that is movable forward and backward in an axial direction and has an endoscope-coupling part and a treatment tool-coupling part is provided inside the outer tube body. The insertion part of the endoscope and the insertion part of the treatment tool are held by the respective coupling parts of the interlocking member in a state where the insertion parts are made to be parallel to each other. If the insertion part of the treatment tool is moved in the axial direction, the insertion part of the endoscope also moves in the axial direction in an interlocking manner with this movement. Accordingly, the number of the holes made in the patient's body wall can be reduced, and the invasion to the patient can be suppressed. In addition, the visual field of the endoscope can be easily changed while an operator operates the treatment tool without asking for an assistant's help.

SUMMARY OF THE INVENTION

Meanwhile, the external diameter of the insertion part of the endoscope or the treatment tool is not necessarily unified. Particularly, as the treatment tool, many types of treatment tools in which applications or manufacturers are different from each other are present, and it is also assumed that the existing treatment tool is replaced with different types of treatment tools during treatment. In that case, it is also considered that the external diameter of the insertion part of a treatment tool that an operator intends to use varies greatly.

However, in the technique that the applicant of the present application has suggested in WO2013/176167A, the coupling between the endoscope or the treatment tool, and the interlocking member presses and holds the insertion part inserted through an O ring of the interlocking member, and insertion parts of which the external diameter is greatly different from the internal diameter of the O ring cannot be used. For that reason, convenience may be impaired in that the types of available endoscopes or treatment tools are limited.

Additionally, an oil component or the like in a living body may adhere to the O ring during treatment. In that case, the holding force of the insertion part of the endoscope or the treatment tool may vary, and the insertion part may move with respect to the O ring irrespective of an operator's unintended action. On the other hand, if an initial holding force is set such that a sufficient holding force is maintained even if an oil component adheres, a situation in which the insertion part does not move with respect to the O-ring may occur irrespective of the operator's intention, for example, immediately after the beginning of use.

The invention has been made in view of such circumstances, and an object thereof is to provide a surgical apparatus for an endoscope and an outer tube that ease limitation of the types of available medical instruments to improve convenience and improve operability.

In order to achieve the above object, a surgical apparatus for an endoscope according to an aspect of the invention is a surgical apparatus for an endoscope comprising a first medical instrument having a first insertion part to be inserted into a body cavity; a second medical instrument having a second insertion part to be inserted into the body cavity; and an outer tube that passes through a body wall, is inserted into the body cavity, and guides the first insertion part and the second insertion part into the body cavity. The outer tube includes an outer tube body having a distal end, a base end, and a longitudinal axis, a first distal end opening and a second distal end opening provided at the distal end of the outer tube body, a first base end opening and a second base end opening provided at the base end of the outer tube body, a first insertion passage that is provided along the longitudinal axis of the outer tube body, allows the first distal end opening and the first base end opening to communicate with each other, and has the first insertion part to be inserted therethrough so as to be movable forward and backward, a second insertion passage that is provided along the longitudinal axis of the outer tube body, allows the second distal end opening and the second base end opening to communicate with each other, and has the second insertion part to be inserted therethrough so as to be movable forward and backward, an interlocking member that has a first coupling part to be coupled to the first insertion part inserted through the first insertion passage and a second coupling part to be coupled to the second insertion part inserted through the second insertion passage, and is movable forward and backward inside the outer tube body, and a fixed member that is provided in at least one coupling part of the first coupling part or the second coupling part, has an inner peripheral surface contacting an entire outer peripheral surface, in a circumferential direction, of an insertion part to be coupled to the at least one coupling part, is made of a foamed elastic body having a number of pores, and makes the pores hold an oil component.

According to this aspect, the medical instrument and the interlocking member are connected (fixed) to each other by bringing an outer peripheral surface of the first insertion part of the first medical instrument or an outer peripheral surface of the second insertion part of the second medical instrument into contact with an inner peripheral surface of the fixed member made of the foamed elastic body. Therefore, even a medical instrument of an insertion part with a relatively larger diameter with respect to the diameter of the inner peripheral surface of the fixed member can be coupled to the interlocking member by the contraction of the fixed member.

Hence, the limitation of the types of available medical instruments can be eased. Additionally, it is also possible to make the external diameter of the fixed member small, and the diameter of the outer tube can be reduced.

Additionally, since the fixed member is made to hold an oil component, even in a case where the oil component or the like in a living body adheres to the fixed member during treatment, fluctuation of a holding force of the medical instrument by the fixed member can be prevented in advance, and operability can be improved.

In the surgical apparatus for an endoscope according to the aspect of the invention, it is possible to adopt an aspect in which the fixed member has a smaller-diameter part formed to have a smaller external diameter than one end part and the other end part thereof in an axial direction between the one end part and the other end part.

According to this aspect, since a medical instrument can be fixed to the fixed member by the combination of a restoring force of the fixed member against contraction and a restoring force of the fixed member against deformation other than the contraction, the holding force of the medical instrument by the fixed member can be increased. Hence, the size of the fixed member can be reduced, and the diameter of the outer tube can also be reduced.

In the surgical apparatus for an endoscope according to the aspect of the invention, it is possible to adopt an aspect in which the first medical instrument is an endoscope in which an observation part is provided at a distal end of the first insertion part, and the second medical instrument is a treatment tool in which a treatment part is provided at a distal end of the second insertion part.

In the surgical apparatus for an endoscope according to the aspect of the invention, it is possible to adopt an aspect in which the fixed member is provided in the second coupling part.

That is, in a case where the second coupling part of the interlocking member is coupled to the treatment tool, the limitation of the types of available treatment tools can be eased, and the use of various treatment tools becomes possible.

In the surgical apparatus for an endoscope according to the aspect of the invention, it is possible to adopt an aspect in which the interlocking member is an interlocking member disposed inside the outer tube body so as to be movable forward and backward, and has a non-sensing region where the forward and backward movement of any one of the first insertion part and the second insertion part does not interlock with the forward and backward movement of the other of the first insertion part and the second insertion part, and a sensing region where the forward and backward movement of any one of the first insertion part and the second insertion part interlocks with the forward and backward movement of the other of the first insertion part and the second insertion part.

According to this aspect, since the endoscope does not move forward and backward, for example, with respect to the forward and backward movement operation of the treatment tool in the non-sensing region, there is an advantage that a stable observation image can be obtained.

Additionally, an outer tube according to another aspect of the invention is an outer tube to be used in a surgical apparatus for an endoscope including a first medical instrument having a first insertion part to be inserted into a body cavity, a second medical instrument having a second insertion part to be inserted into the body cavity, and an outer tube that passes through a body wall, is inserted into the body cavity, and guides the first insertion part and the second insertion part into the body cavity. The outer tube comprises an outer tube body having a distal end, a base end, and a longitudinal axis; a first distal end opening and a second distal end opening provided at the distal end of the outer tube body; a first base end opening and a second base end opening provided at the base end of the outer tube body; a first insertion passage that is provided along the longitudinal axis of the outer tube body, allows the first distal end opening and the first base end opening to communicate with each other, and has the first insertion part to be inserted therethrough so as to be movable forward and backward; a second insertion passage that is provided along the longitudinal axis of the outer tube body, allows the second distal end opening and the second base end opening to communicate with each other, and has the second insertion part to be inserted therethrough so as to be movable forward and backward; an interlocking member that has a first coupling part to be coupled to the first insertion part inserted through the first insertion passage and a second coupling part to be coupled to the second insertion part inserted through the second insertion passage, and is movable forward and backward inside the outer tube body; and a fixed member that is provided in at least one coupling part of the first coupling part or the second coupling part, has an inner peripheral surface contacting an entire outer peripheral surface, in a circumferential direction, of an insertion part to be coupled to the at least one coupling part, is made of a foamed elastic body having a number of pores, and makes the pores hold an oil component.

According to this aspect, the medical instrument and the interlocking member are connected (fixed) to each other by bringing an outer peripheral surface of the first insertion part of the first medical instrument or an outer peripheral surface of the second insertion part of the second medical instrument into contact with an inner peripheral surface of the fixed member made of the foamed elastic body. Accordingly, even a medical instrument of an insertion part with a relatively larger diameter with respect to the diameter of the inner peripheral surface of the fixed member can be coupled to the interlocking member by the contraction of the fixed member.

Hence, the limitation of the types of available medical instruments can be eased. Additionally, it is also possible to make the external diameter of the fixed member small, and the diameter of the outer tube can be reduced.

Additionally, since the fixed member is made to hold an oil component, even in a case where the oil component or the like in a living body adheres to the fixed member during treatment, fluctuation of a holding force of the medical instrument by the fixed member can be prevented in advance. As a result, operability can be improved.

In the outer tube according to the other aspect of the invention, it is possible to adopt an aspect in which the fixed member has a smaller-diameter part formed to have a smaller external diameter than one end part and the other end part thereof in an axial direction between the one end part and the other end part.

According to this aspect, since a medical instrument can be fixed to the fixed member by the combination of a restoring force of the fixed member against contraction and a restoring force of the fixed member against deformation other than the contraction, the holding force of the medical instrument by the fixed member can be increased. Hence, the size of the fixed member can be reduced, and the diameter of the outer tube can also be reduced.

In the outer tube according to the other aspect of the invention, it is possible to adopt an aspect in which the first medical instrument is an endoscope in which an observation part is provided at a distal end of the first insertion part, and the second medical instrument is a treatment tool in which a treatment part is provided at a distal end of the second insertion part.

In the outer tube according to the other aspect of the invention, it is possible to adopt an aspect in which the fixed member is provided in the second coupling part.

That is, in a case where the second coupling part of the interlocking member is coupled to the treatment tool, the limitation of the types of available treatment tools can be eased, and the use of various treatment tools becomes possible.

In the outer tube according to the other aspect of the invention, it is possible to adopt an aspect in which the interlocking member is an interlocking member disposed inside the outer tube body so as to be movable forward and backward, and has a non-sensing region where the forward and backward movement of any one of the first insertion part and the second insertion part does not interlock with the forward and backward movement of the other of the first insertion part and the second insertion part, and a sensing region where the forward and backward movement of any one of the first insertion part and the second insertion part interlocks with the forward and backward movement of the other of the first insertion part and the second insertion part.

According to this aspect, since the endoscope does not move forward and backward, for example, with respect to the forward and backward movement operation of the treatment tool in the non-sensing region, there is an advantage that a stable observation image can be obtained.

According to the invention, convenience can be improved and operability can be improved by easing the limitation of the types of available medical instruments.

DESCRIPTION OF THE PREFERRED EMBODIMENTS

Preferred embodiments of the invention will be described below in detail according to the accompanying drawings. In addition, any of the drawings may illustrate main parts in an exaggerated manner for description, and may have dimensions different from actual dimensions.

Figure 1:
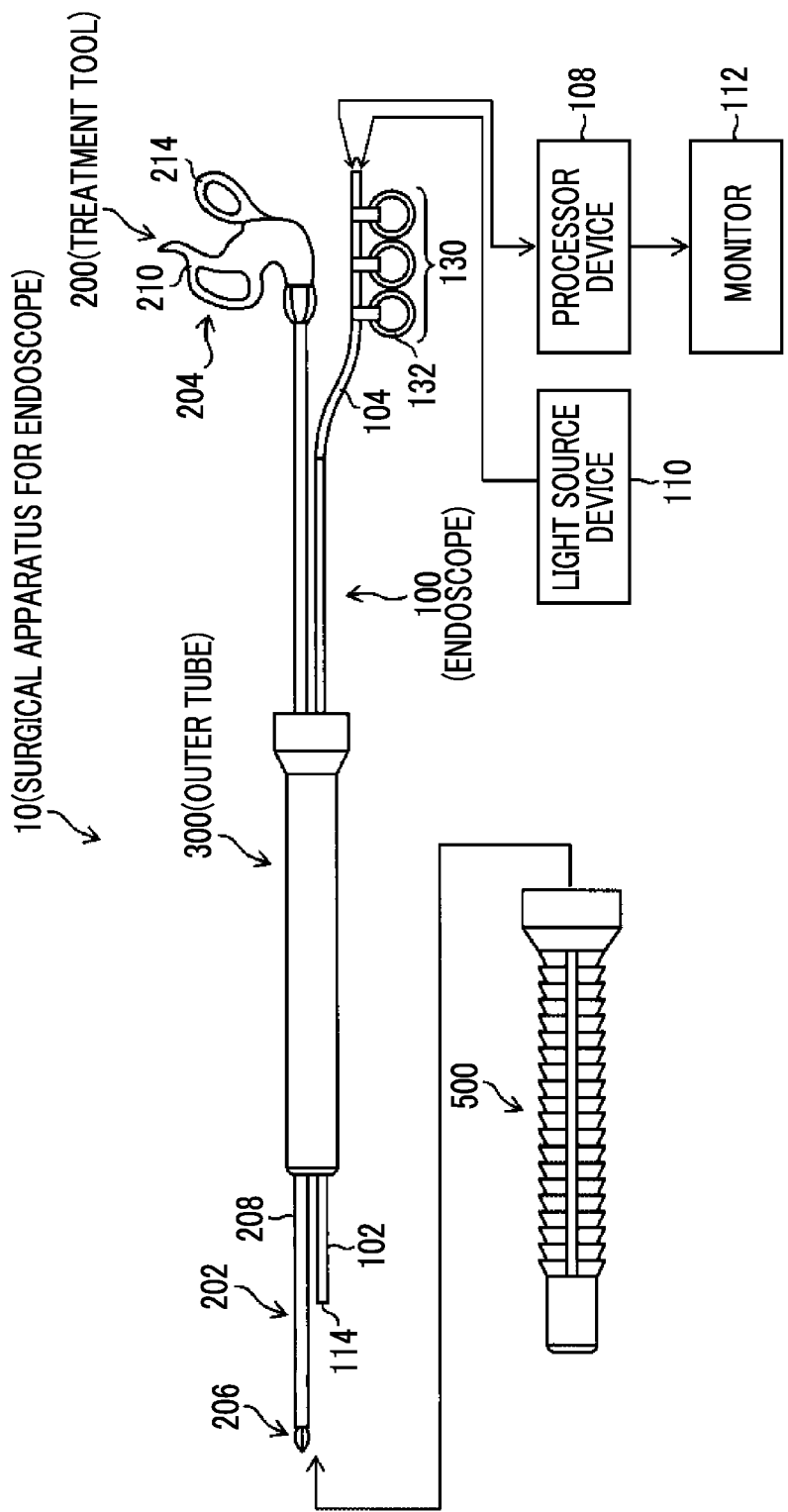
FIG. 1 is a schematic block diagram of a surgical apparatus for an endoscope according to the invention.

FIG. 1 is a schematic block diagram of a surgical apparatus for an endoscope according to the invention. As illustrated in FIG. 1, a surgical apparatus for an endoscope 10 includes an endoscope 100 that observes the inside of a patient's body cavity, a treatment tool 200 for examining or treating a diseased site within the patient's body cavity, an outer tube 300 that is inserted into a body wall and guides the endoscope 100 and the treatment tool 200 into the body cavity, and an exterior tube 500 fitted to the outer tube 300.

The endoscope 100 is, for example, a hard endoscope, such as a laparoscope, and includes an insertion part 102 (hereinafter referred to as "endoscope insertion part 102") that is inserted into a body cavity, and that has an outer peripheral part surrounded by an elongated hard tubular body, and a cable part 104 that is provided continuously with a base end side of the endoscope insertion part 102 and that has an outer peripheral part surrounded by an elongated flexible tubular body.

The cable part 104 indicates a flexible cable portion in which a wire rod, such as a cable or a light guide, which extends from a base end of the endoscope insertion part 102, is housed by covering the wire rod with, for example, a flexible insulating member, such as polyvinyl chloride.

A connector (not illustrated) is provided at an end of the cable part 104 on its extension destination, and each of a processor device 108 and a light source device 110 is detachably connected to the cable part via the connector. Additionally, the processor device 108 is connected to a monitor 112 via a cable.

Figure 2:
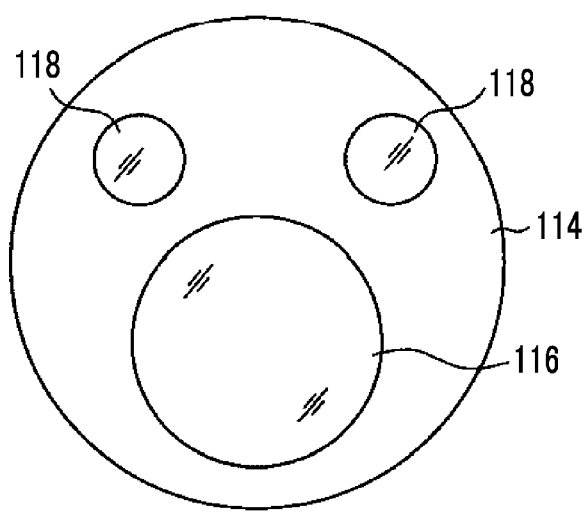
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

The observation window 116 is a constituent element of an observation part of the endoscope 100, and an objective lens of an observation optical system, and a solid image pickup element, such as a charge coupled device (CCD) image sensor or a complementary metal oxide semiconductor (CMOS) image sensor, which is disposed at an image pickup position of the objective lens, are disposed behind the observation window 116. A signal cable (not illustrated) connected to this solid image pickup element is inserted through the endoscope insertion part 102 and the cable part 104 of FIG. 1, is provided to extend up to the connector (not illustrated), and is connected to the processor device 108. An observation image picked up from the observation window 116 is formed on a light-receiving surface of the image pickup element, and is converted into electrical signals (image pickup signals), and the electrical signals are output to the processor device 108 via the signal cable and are converted into video signals. Then, the video signals are output to the monitor 112 connected to the processor device 108, and the observation image (endoscopic image) is displayed on a screen of the monitor 112.

An exit end of the light guide (not illustrated) is disposed behind the illumination windows 118 and 118 of FIG. 2. The light guide is inserted through the endoscope insertion part 102 and the cable part 104 of FIG. 1 and has an incident end disposed within the connector (not illustrated). Hence, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of illumination windows 118 is not limited, and the number thereof may be one or may be three or more.

Addition, as illustrated in FIG. 1, the cable part 104 of the endoscope 100 is provided with a forward and backward movement operating part 130 for hooking the index finger of a right hand gripping an operating part 204 of the treatment tool 200, and performing a forward and backward movement operation of the endoscope 100 in a forward-backward direction of the endoscope 100.

The forward and backward movement operating part 130 is disposed at a position adjacent to the operating part 204 of the treatment tool 200, and has, for example, three hooking parts 132 of the same configuration. Each hooking part 132 is formed in an annular shape (ring shape) using elastic materials (for example, rubber materials), and has an opening of such a size that an index finger can pass therethrough.

Accordingly, an operator can pass the index finger of his/her right hand gripping the operating part 204 of the treatment tool 200, through any hooking part 132 of the forward and backward movement operating part 130 to perform the forward and backward movement operation of the endoscope 100, and can easily perform the operation of the treatment tool 200 and the forward and backward movement operation of the endoscope 100 only with his/her right hand. In addition, the endoscope 100 may not include the forward and backward movement operating part 130, and the detailed description of the forward and backward movement operating part 130 will be omitted.

As illustrated in FIG. 1, the treatment tool 200 consists of, for example, forceps, and includes an elongated insertion part 202 (hereinafter referred to as a "treatment tool insertion part 202") that is inserted into a body cavity, an operating part 204 that is provided on the base end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is turnably coupled to the fixed handle 210 via a turning pin. A base end part of the operating shaft is coupled to the movable handle 214.

The treatment part 206 is provided with a pair of gripping members that is operable and closable. The gripping members are coupled to a distal end part of the operating shaft via a driving mechanism (not illustrated). With the turning operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, an ultrasonic device, and an aspirator.

As illustrated in FIG. 1, the outer tube 300 allows the endoscope insertion part 102 and the treatment tool insertion part 202, which are inserted thereinto from the base end side, to be inserted therethrough and delivered from the distal end side. By inserting the outer tube 300 into a body wall and having a base end side thereof disposed outside of the body and a distal end side thereof disposed within the body cavity, the endoscope insertion part 102 and the treatment tool insertion part 202 are guided into the body cavity with one outer tube 300. Additionally, the outer tube 300 includes an interlocking function of moving the endoscope insertion part 102 and the treatment tool insertion part 202 forward and backward in an interlocking manner as will be described below in detail. Accordingly, for example, the endoscope insertion part 102 can also be moved forward and backward by the forward and backward movement operation of only the treatment tool insertion part 202, and a suitable observation image can be obtained without performing the forward and backward movement operation of the endoscope insertion part 102. The details of the configuration and working of the outer tube 300 will be described below.

Figure 3:
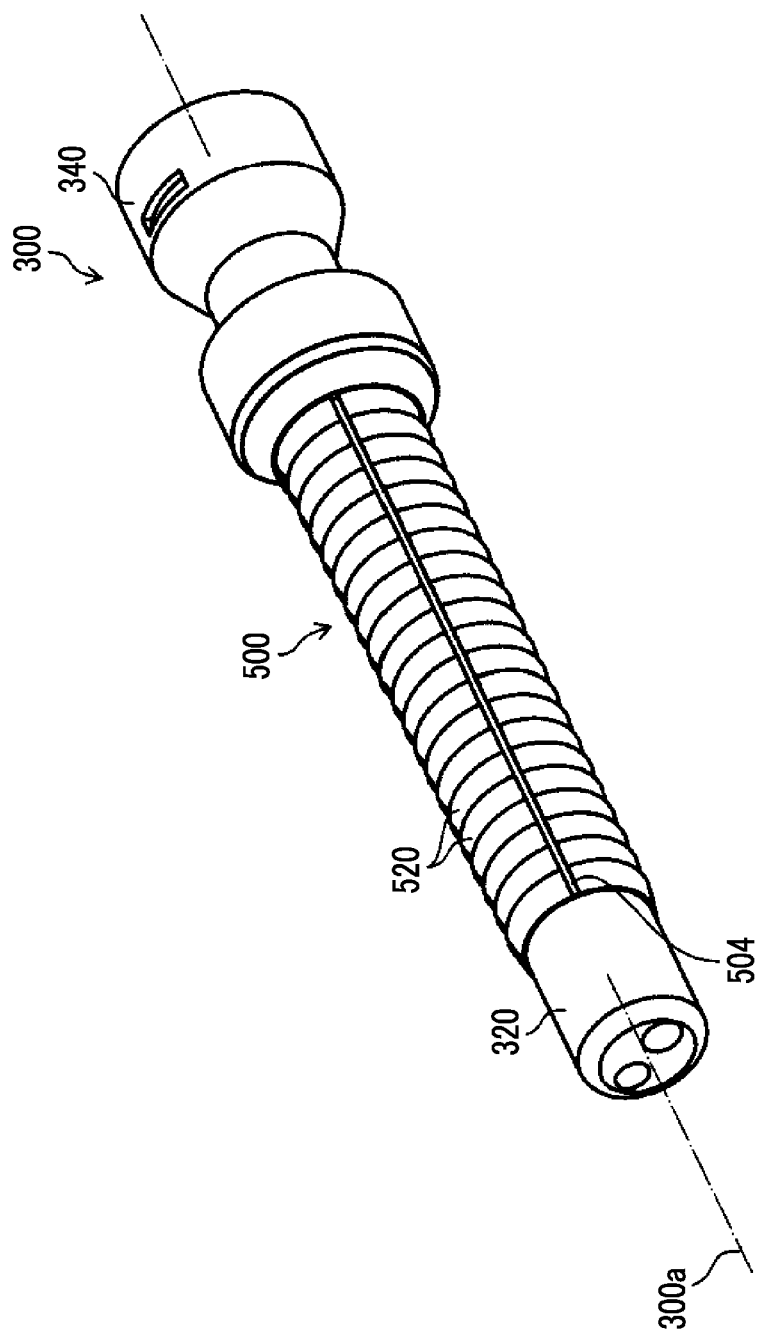
FIG. 3 is a perspective view illustrating a state where an exterior tube is fitted to an outer tube.

The exterior tube 500 illustrated in FIG. 1 is formed in a tubular shape, and as illustrated in FIG. 3, is externally fitted (sheathed) to and fixed to an outer peripheral surface of the outer tube 300 (a long tubular outer tube body 320 to be described below). Although detailed description is omitted, an outer peripheral part of the exterior tube 500 is provided with a number of lateral grooves 520 running along in a circumferential direction, and longitudinal grooves 504 running along an axial direction are provided, for example, in four places in the circumferential direction.

Accordingly, in a state where the outer tube 300 is inserted into a body wall together with the exterior tube 500, a number of the lateral grooves 520 of the exterior tube 500 restrict the forward and backward movement of the exterior tube 500 with respect to the body wall, and the longitudinal grooves in four places of the exterior tube 500 restrict the rotation of the exterior tube 500 in the circumferential direction (around a reference axis 300a) with respect to the body wall. Hence, unintended rotation or forward and backward movement of the outer tube 300 fixed to the exterior tube 500 with respect to the body wall is prevented.

Namely, if the outer tube 300 rotates around the reference axis 300a (around the axis) unintentionally with respect to the body wall or moves forward and backward in the direction (axial direction) of the reference axis 300a when the operation of the treatment tool 200, or the like is performed by inserting the endoscope insertion part 102 and the treatment tool insertion part 202 through the outer tube 300 after the outer tube 300 (long tubular outer tube body 320) is inserted into the body wall, there is a problem that the position of a distal end of the endoscope insertion part 102 may fluctuate and an observation visual field may fluctuate unintentionally. The exterior tube 500 prevents such unintended fluctuation of the observation visual field.

Figure 4:
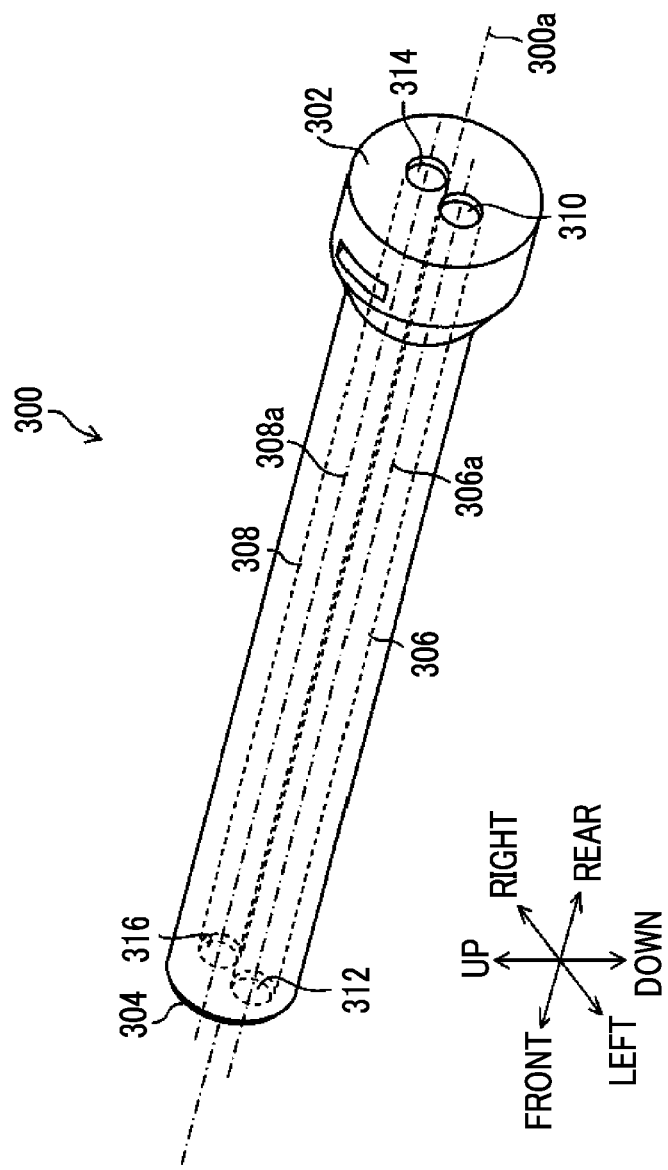
FIG. 4 is an external perspective view illustrating the outer tube.

FIG. 4 is an external perspective view illustrating the outer tube 300.

As illustrated in this drawing, the outer tube 300 has an elongated cylindrical shape as a whole, and has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward. These insertion passages are parallel to a reference axis 300a indicating a longitudinal axis that is a central axis of the outer tube.

If a central axis of the endoscope insertion passage 306 is referred to as an endoscope insertion axis 306a and a central axis of the treatment tool insertion passage 308 is referred to as a treatment tool insertion axis 308a, the endoscope insertion axis 306a and the treatment tool insertion axis 308a are parallel to each other, and is also parallel to the reference axis 300a. The endoscope insertion axes 306a and the treatment tool insertion axes 308a are equivalent to positions of the central axis of the endoscope insertion part 102 and the central axis of the treatment tool insertion part 202 that are respectively inserted through the endoscope insertion passage 306 and the treatment tool insertion passage 308. Additionally, in the present embodiment, the reference axis 300a, the endoscope insertion axis 306a, and the treatment tool insertion axis 308a are disposed on the same plane. However, a configuration in which the reference axis 300a, the endoscope insertion axis 306a, and the treatment tool insertion axis 308a are disposed on the same plane may not be adopted.

In addition, regarding the position and orientation of a space where the outer tube 300 has been disposed, terms called forward, backward, left, right, up, and down are used with the orientation from the base end surface 302 in a direction along the reference axis 300a to the distal end surface 304 defined as the forward and with the orientation from the reference axis 300a to the endoscope insertion axis 306a defined as the left.

The base end surface 302 of the outer tube 300 is provided with a first base end opening 310 that is a base end opening that allows the endoscope insertion part 102 to be inserted into the endoscope insertion passage 306 therethrough, and a second base end opening 314 that is base end opening that allows the treatment tool insertion part 202 to be inserted into the treatment tool insertion passage 308 therethrough.

The distal end surface 304 of the outer tube 300 is provided with a first distal end opening 312 that is a distal end opening that allows the endoscope insertion part 102 inserted into the endoscope insertion passage 306 to be delivered to the outside therethrough, and a second distal end opening 316 that is a distal end opening that allows the treatment tool insertion part 202 inserted into the treatment tool insertion passage 308 to be delivered to the outside therethrough.

Figure 5:
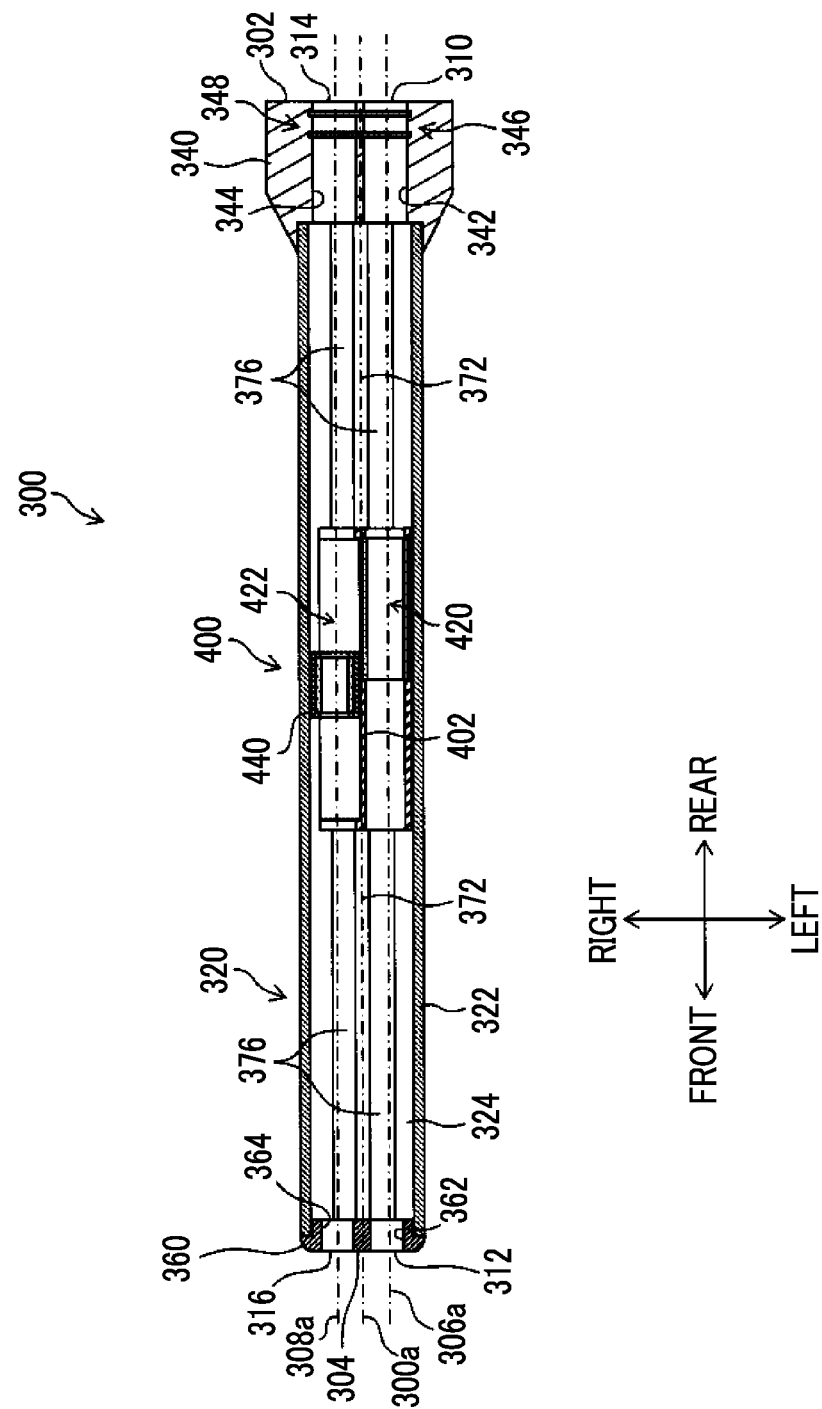
FIG. 5 is a cross sectional view illustrating the internal structure of the outer tube.

FIG. 5 is a cross sectional view illustrating the internal structure of the outer tube 300, and illustrates a cross section cut in a plane that includes the reference axis 300a and is orthogonal to an upward-downward direction (cut in a leftward-rightward direction along the reference axis 300a).

As illustrated in this drawing, the outer tube 300 has a long tubular outer tube body 320 that occupies substantially the entire area in the forward-backward direction, a base end cap 340 that is attached to a rear end (base end) of the outer tube 300, a distal end cap 360 that is attached to a distal end part, and a slider 400 that is one form of the interlocking member disposed inside the outer tube 300.

The long tubular outer tube body 320 is formed in an elongated cylindrical shape having the reference axis 300a as a central axis using hard resins, metals, or the like, and has an outer wall 322 that surrounds an outer periphery, and a cavity part 324 that penetrates from a base end of the long tubular outer tube body 320 to a distal end thereof The cavity part 324 includes spaces serving as the endoscope insertion passage 306 and the treatment tool insertion passage 308, and houses the slider 400 and the like.

The base end cap 340 is formed in a columnar shape of which the diameter is made larger than the external diameter of the long tubular outer tube body 320 using hard resins, metals, or the like, and a rear end surface thereof constitutes the base end surface 302 of the outer tube 300. The base end cap 340 is provided with a through-hole 342 and a through-hole 344 that form a portion of the endoscope insertion passage 306 and a portion of the treatment tool insertion passage 308, respectively. In the base end surface 302, an opening of the through-hole 342 is equivalent to the above-described first base end opening 310, and an opening of the through-hole 344 is equivalent to the above-described second base end opening 314.

Additionally, the through-holes 342 and 344 are provided with valve members 346 and 348. The valve members 346 and 348, for example, open only in a case where the endoscope insertion part 102 and the treatment tool insertion part 202 are inserted therethrough and come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 is formed of hard resins, metals, or the like, and a distal end surface thereof constitutes the distal end surface 304 of the outer tube 300. The distal end cap 360 is provided with a through-hole 362 and a through-hole 364 that form a portion of the endoscope insertion passage 306 and a portion of the treatment tool insertion passage 308, respectively. In the distal end surface 304, an opening of the through-hole 362 is equivalent to the above-described first distal end opening 312, and an opening of the through-hole 364 is equivalent to the second distal end opening 316.

In addition, the long tubular outer tube body 320, the base end cap 340, and the distal end cap 360 show one form of constituent members that constitutes the outer tube body of the outer tube 300, and the outer tube body is not limited to the above configuration. For example, the long tubular outer tube body 320 and the base end cap 340 or the long tubular outer tube body 320 and the distal end cap 360 may be integrally formed, or may be integrally formed in their entirety.

Additionally, the outer tube body may have the following configurations.

Namely, the outer tube body has a distal end, a base end, and a longitudinal axis, and includes a first distal end opening and a second distal end opening equivalent to the above-described first distal end opening 312 and second distal end opening 316 that are provided at the distal end of the outer tube body, and a first base end opening and a second base end opening equivalent to the above-described first base end opening 310 and the second base end opening 314 that are provided at the base end of the outer tube body. The outer tube body just has to include an endoscope insertion passage and a treatment tool insertion passage equivalent to the above-described endoscope insertion passage 306 and treatment tool insertion passage 308 that are provided along the longitudinal axis of the outer tube body, that is, the endoscope insertion passage that communicates with the first distal end opening and the first base end opening and allows the endoscope 100 to be inserted therethrough so as to be movable forward and backward, and the treatment tool insertion passage that communicates with the second distal end opening and the second base end opening and allows the treatment tool 200 to be inserted therethrough so as to be movable forward and backward.

The slider 400 is housed within (the cavity part 324) the long tubular outer tube body 320, and is supported so as to be movable forward and backward in the direction of the reference axis 300a. The slider 400 is an interlocking member that is coupled to the endoscope insertion part 102 inserted through the endoscope insertion passage 306 and the treatment tool insertion part 202 inserted through the treatment tool insertion passage 308 and that has a non-sensing region where the forward and backward movement of either the endoscope insertion part or the treatment tool insertion part in the forward-backward direction (axial direction) does not interlock with the movement of the other and a sensing region where the forward and backward movement of either the endoscope insertion part or the treatment tool insertion part interlocks with the movement of the other. That is, the endoscope insertion part 102 is adapted to interlock with the forward and backward movement of the treatment tool insertion part 202 in the axial direction with play by the slider 400.

Figure 6:
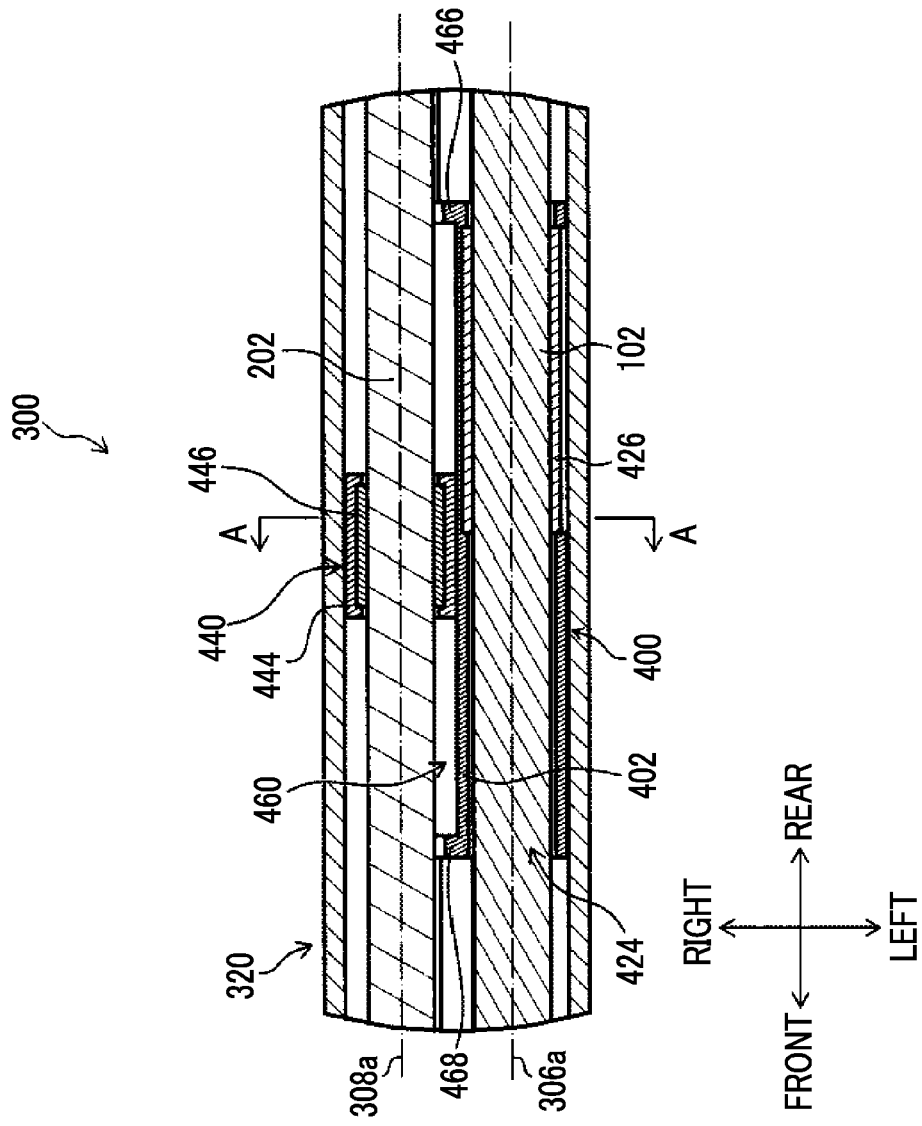
FIG. 6 is an enlarged cross sectional view illustrating a portion of FIG. 5 in an enlarged manner.
Figure 7:
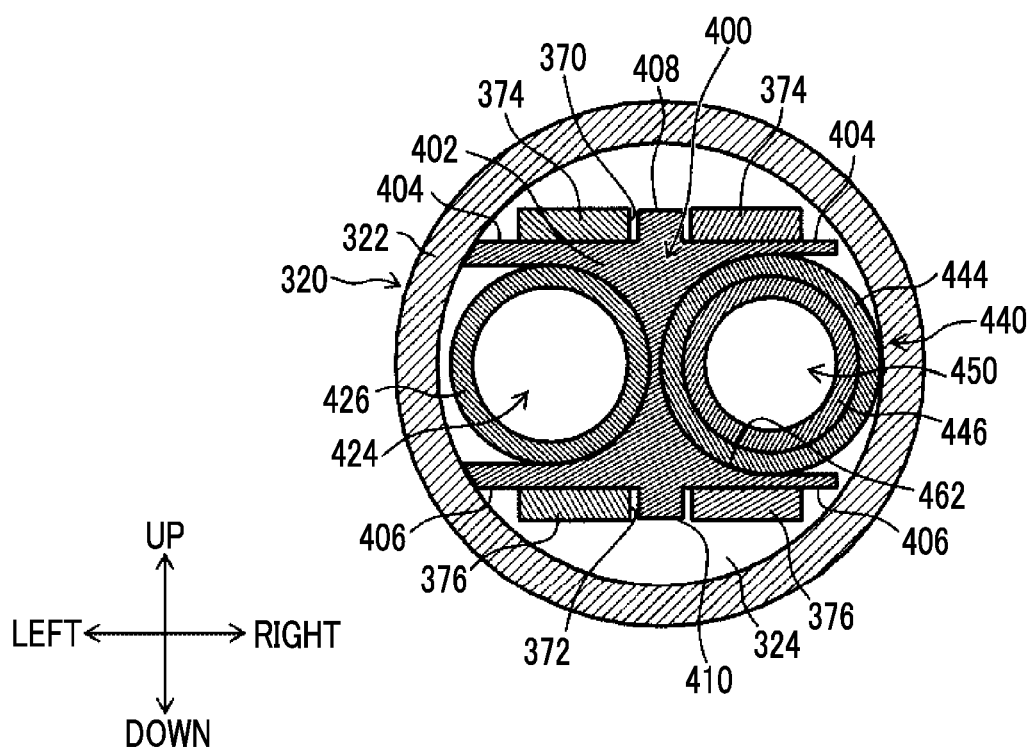
FIG. 7 is a cross sectional view as viewed from arrow A-A in FIG. 6.

FIG. 6 is an enlarged cross sectional view illustrating a portion, in which the slider 400 is disposed in FIG. 5, in an enlarged manner, and illustrates a state where the endoscope insertion part 102 and the treatment tool insertion part 202 have been inserted through the endoscope insertion passage 306 and the treatment tool insertion passage 308, respectively. FIG. 7 is a cross sectional view as seen from arrow A-A in FIG. 6.

Figure 8:
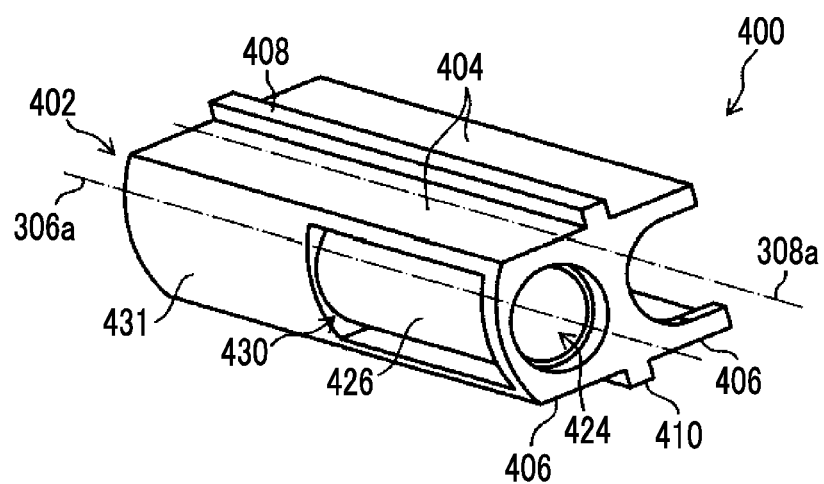
FIG. 8 is a perspective view illustrating a slider (interlocking member) from the rear upper left side.
Figure 9:
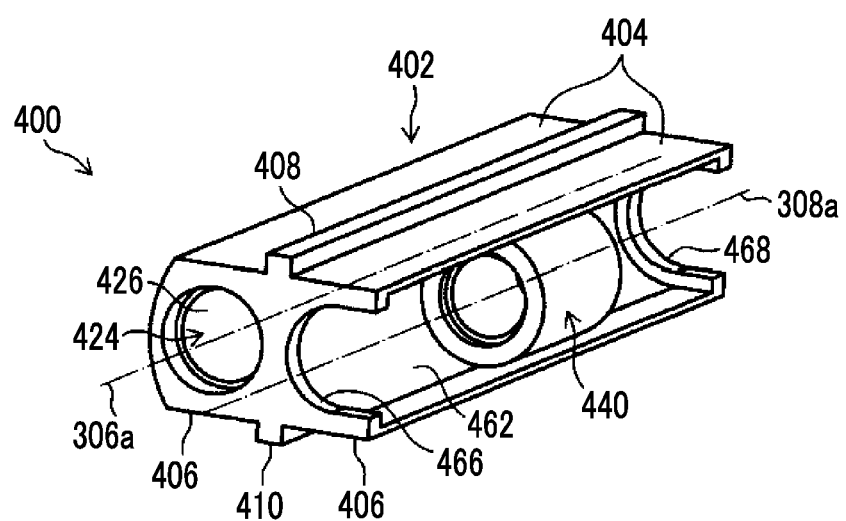
FIG. 9 is a perspective view illustrating the slider (interlocking member) from the rear upper right side.

Additionally, FIGS. 8 and 9 are respectively perspective views illustrating the slider 400 from the rear upper left and from the rear upper right.

As illustrated in these drawings, the slider 400 has a slider body 402 that holds components of the slider 400. As illustrated in FIG. 7, protruding strips 408 and 410 that extend in the direction (forward-backward direction) of the reference axis 300a are formed on a flat upper surface 404 (refer to FIGS. 8 and 9) and a flat lower surface 406 of the slider body 402.

Meanwhile, a pair of left and right long plate-shaped guide plates 374 and 374 and a pair of left and right long plate-shaped guide plates 376 and 376, which are laid between the base end cap 340 and the distal end cap 360 and illustrated in FIG. 7, are respectively supported by an upper part and a lower part within the long tubular outer tube body 320, and guide grooves 370 and 372, which extend in the direction of the reference axis 300a from the base end cap 340 to the distal end cap 360, are formed by a gap between the guide plates 374 and 374 and a gap between the guide plates 376 and 376.

The protruding strips 408 and 410 of the slider body 402 are respectively fitted into the guide grooves 370 and 372 within the long tubular outer tube body 320, and the upper surface 404 and the lower surface 406 are disposed in a state where these surfaces have contacted or approached the guide plates 374 and 374 and the guide plates 376 and 376.

Accordingly, the slider 400 is supported so as to be movable forward and backward in the forward-backward direction within the long tubular outer tube body 320, and is supported in a state where the movement of the slider in the upward-downward direction and in the leftward-rightward direction and the rotation of the slider in all directions (directions around three axes including a forward-backward axis, a leftward-rightward axis, and an upward-downward direction) are restricted (a state where the rotation of the slider around at least the reference axis 300a is impossible). Additionally, the slider 400 moves forward and backward within a movable range having a position where the slider abuts against the base end cap 340 as a rear end, and having a position where the slider abuts against the distal end cap 360 as a front end.

In addition, the guide grooves 370 and 372 may not be formed by the guide plates 374 and 374 and the guide plates 376 and 376 disposed within the long tubular outer tube body 320, and may be formed in the outer wall 322 of the long tubular outer tube body 320 or may be formed by other configurations.

Additionally, the slider 400, as illustrated in FIG. 5, has a left endoscope-coupling part 420 that is coupled to (engaged with) the endoscope insertion part 102, and a right treatment tool-coupling part 422 that is coupled to (engaged with) the treatment tool insertion part 202.

The endoscope-coupling part 420 provided on the left side of the slider body 402 secures a space serving as the endoscope insertion passage 306, within the long tubular outer tube body 320. Additionally, the endoscope-coupling part 420, as illustrated in FIG. 6, includes a through-hole 424 (refer to FIGS. 7, 8, and 9) into which the endoscope insertion part 102 is inserted, and a pressure-contact member 426 serving as a fixed member that is fixed to the through-hole 424 and is brought into pressure contact with the outer peripheral surface (side surface) of the endoscope insertion part 102 inserted through the endoscope insertion passage 306.

The pressure-contact member 426 is formed in a cylindrical shape using elastic materials as illustrated in FIGS. 7 and 8. The pressure-contact member 426 is fitted into up to a position coaxial with the through-hole 424 of the slider body 402 from an opening 430 formed on a left side surface 431 of the slider body 402 and fixed to the slider body 402, as illustrated in FIG. 8.

Accordingly, when the endoscope insertion part 102 has been inserted through the endoscope insertion passage 306, as illustrated in FIG. 6, the endoscope insertion part 102 is inserted through the through-hole 424, and the pressure-contact member 426 is brought into pressure contact with (engaged with) the outer peripheral surface of the endoscope insertion part 102. Accordingly, the central axis of the endoscope insertion part 102 is disposed coaxially with the endoscope insertion axis 306a.

The endoscope insertion part 102 and the slider 400 (slider body 402) are coupled to (engaged with) each other in an interlockable manner via the pressure-contact member 426, and the slider 400 (slider body 402) also integrally moves forward and backward in an interlocking manner with the forward and backward movement of the endoscope insertion part 102 in the forward-backward direction (axial direction).

In addition, since the coupling herein is based on the elastic force of the pressure-contact member 426, the engagement position (the position of the endoscope insertion part 102 where the slider 400 is engaged) of the endoscope insertion part 102 coupled to the slider 400 (slider body 402) can be arbitrarily adjusted.

The treatment tool-coupling part 422 provided on the right side of the slider body 402 as illustrated in FIG. 5, as illustrated in FIG. 6, includes a sleeve 440 (refer to FIGS. 7 and 9) that is coupled to the treatment tool insertion part 202, and a guide part 460 that guides the sleeve 440 so as to be movable forward and backward in the forward-backward direction.

The sleeve 440, as illustrated in FIG. 7, includes a sleeve body 444 (frame body) formed in a cylindrical shape, and a pressure-contact member 446 serving as the fixed member fixed to the inside of the sleeve body 444. The pressure-contact member 446 is formed in a cylindrical shape using elastic materials.

Accordingly, when the treatment tool insertion part 202 has been inserted through the treatment tool insertion passage 308, as illustrated in FIG. 6, the treatment tool insertion part 202 is inserted through the inside (the through-hole 450 of FIG. 7) of the pressure-contact member 446, the pressure-contact member 446 is brought into pressure contact with (engaged with) the outer peripheral surface of the treatment tool insertion part 202. Accordingly, the central axis of the treatment tool insertion part 202 is disposed coaxially with the treatment tool insertion axis 308a.

The treatment tool insertion part 202 and the sleeve 440 are coupled to each other in an interlockable manner via the pressure-contact member 446, and the sleeve 440 also integrally moves forward and backward in an interlocking manner with the forward and backward movement of the treatment tool insertion part 202 in the forward-backward direction (axial direction).

Additionally, the sleeve 440 also rotates with respect to the slider body 402 in an interlocking manner with the rotation of the treatment tool insertion part 202 around the axis thereof.

In addition, since the coupling between the treatment tool insertion part 202 and the sleeve 440 herein is based on the elastic force of the pressure-contact member 446, the engagement position (the position of the treatment tool insertion part 202 where the sleeve 440 is engaged) of the treatment tool insertion part 202 coupled to the sleeve 440 can be arbitrarily adjusted.

Meanwhile, the guide part 460 of the treatment tool-coupling part 422, as illustrated in FIGS. 7 and 9, is formed by a space surrounded by a guide surface 462 of the slider body 402 that extends in the direction of the reference axis 300a (treatment tool insertion axis 308a), within the cavity part 324 of the long tubular outer tube body 320, and an inner peripheral surface of the long tubular outer tube body 320. The sleeve 440 is housed and disposed in the space of the guide part 460, is supported so as to be movable in the forward-backward direction and rotatable around its axis, and is supported in a state where the movement of the sleeve in the upward-downward direction and in the leftward-rightward direction is restricted.

Additionally, the guide part 460 is provided so as to fall within a range from a base end of the slider body 402 to a distal end thereof, and as illustrated in FIGS. 6 and 9, has end edge parts 466 and 468, which are formed to protrude in a direction orthogonal to the guide surface 462 along an end edge of the guide surface 462, respectively, on the base end side and the distal end side of the slider body 402.

The end edge parts 466 and 468 abut against the end of the sleeve 440 to restrict the movement of the sleeve 440, when the sleeve 440 disposed in the space of the guide part 460 moves forward and backward in the forward-backward direction.

Hence, the sleeve 440 moves forward and backward within a movable range having a position where the sleeve abuts against the end edge part 466 as a rear end, and having a position where the sleeve abuts against the end edge part 468 as a front end. However, the rear end and the front end of the movable range of the sleeve 440 may not be restricted by the end edge part 466 and the end edge part 468.

The working of the slider 400 configured as described above will be described together with the operation when the treatment of a diseased site within a patient's body cavity is performed using the surgical apparatus for an endoscope 10.

Figure 13:
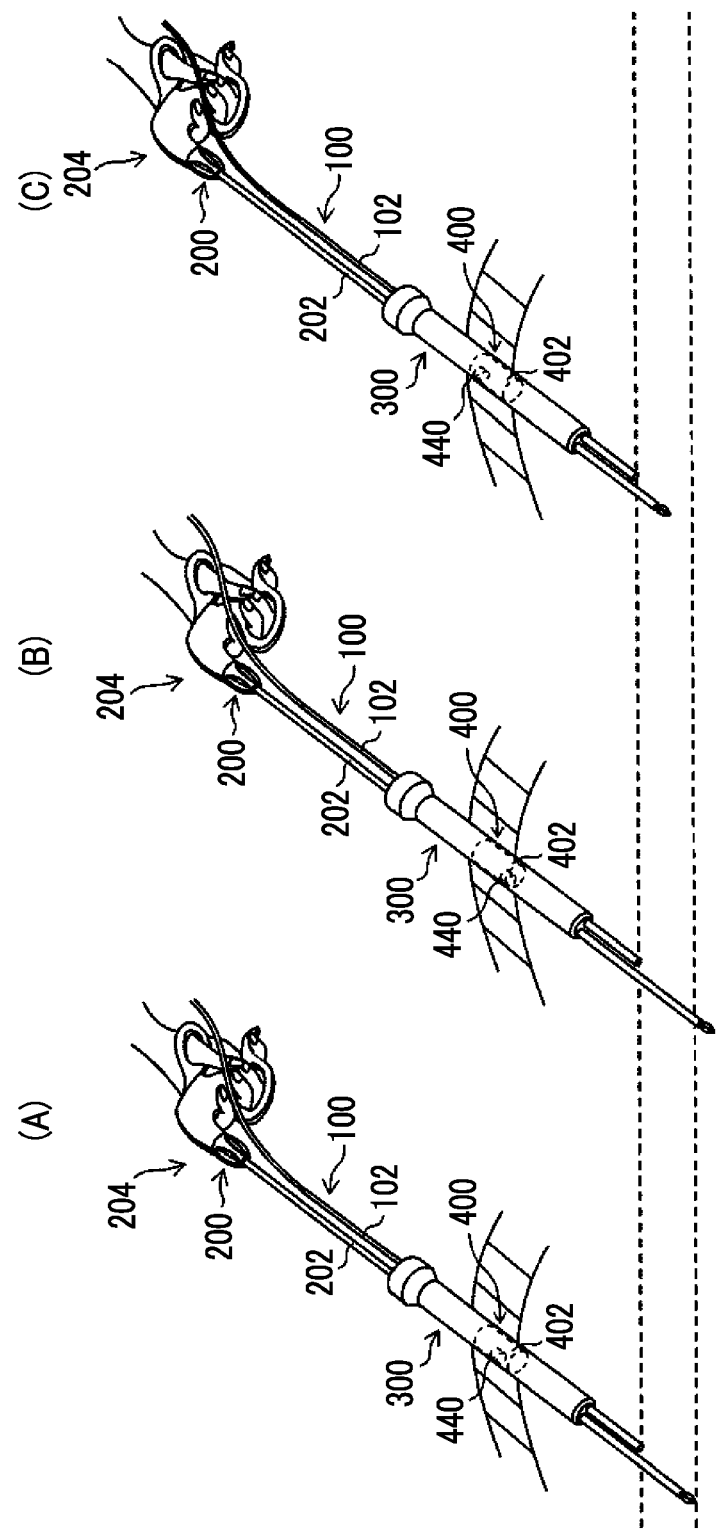
FIG. 13 is an explanatory view illustrating a state of the operation when the treatment of a diseased site within a patient's body cavity is performed using the surgical apparatus for an endoscope.
Figure 14:
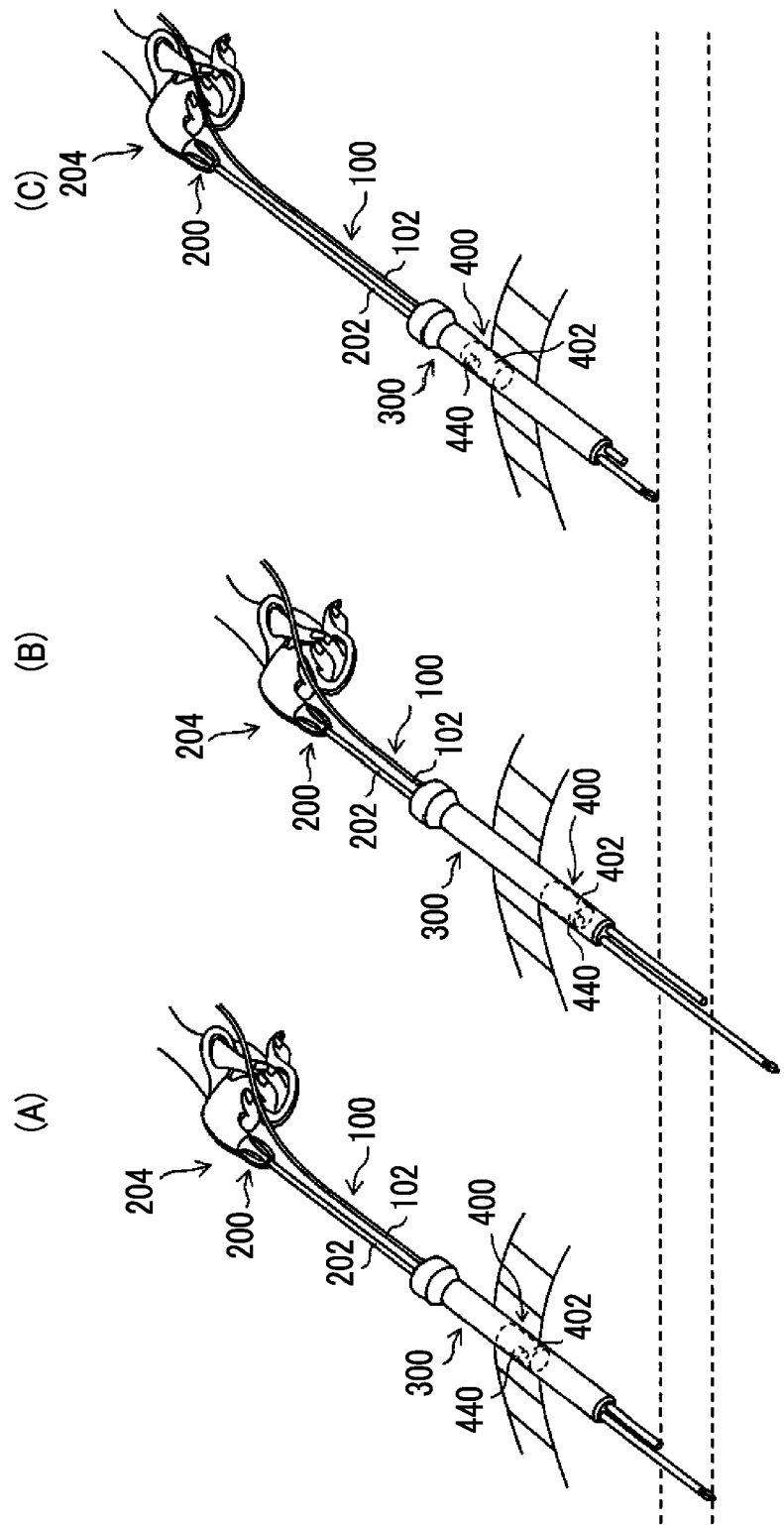
FIG. 14 is an explanatory view illustrating a state of the operation when the treatment of the diseased site within the patient's body cavity is performed using the surgical apparatus for an endoscope.

First, as illustrated in (A) part of FIG. 13, after the outer tube 300 is inserted into a patient's body wall and a pneumoperitoneum gas is injected into a body cavity, the endoscope 100 (endoscope insertion part 102) and the treatment tool 200 (treatment tool insertion part 202) are respectively inserted into the endoscope insertion passage 306 and the treatment tool insertion passage 308 of the outer tube 300, and the endoscope insertion part 102 and the treatment tool insertion part 202 are mounted on the outer tube 300. In this case, the endoscope insertion part 102 is coupled to the slider body 402 of the slider 400, and the treatment tool insertion part 202 is coupled to the sleeve 440 of the slider 400. In addition, although the exterior tube 500 is not illustrated in FIG. 13, and FIG. 14 illustrated therebelow, the exterior tube 500 is fitted to the outer tube 300 as illustrated in FIG. 3. However, it is also possible to use the outer tube 300 without fitting the exterior tube 500 thereto.

Additionally, the forward and backward movement operating part 130 of the endoscope 100 is also omitted in the drawings.

Figure 10:
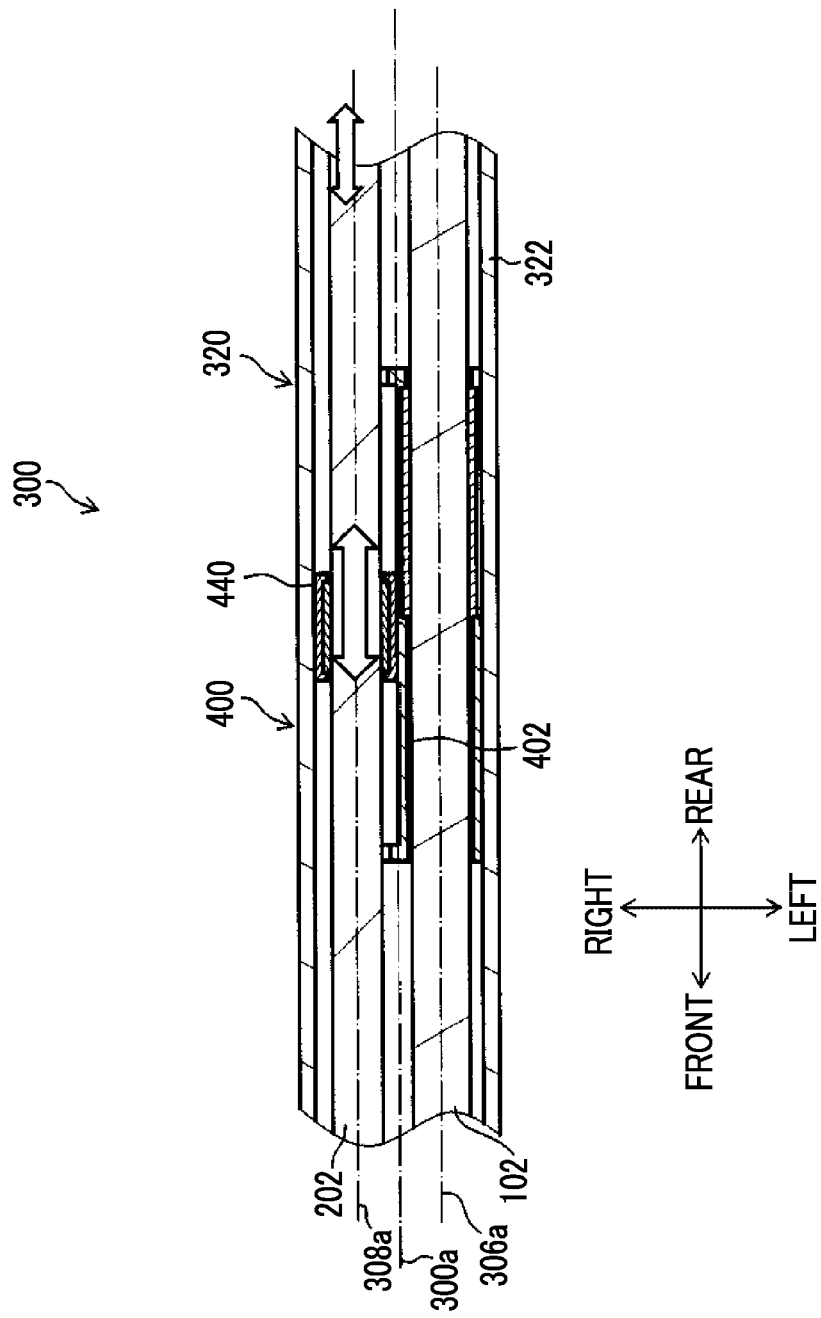
FIG. 10 is an explanatory view used for the description of the working of the slider (interlocking member).

Supposing the state of (A) part of FIG. 13 is a state where the sleeve 440 reaches neither the front end nor the rear end of the movable range thereof with respect to the slider body 402 (guide part 460) as illustrated in FIG. 10, and if an operator minutely moves the treatment tool insertion part 202 forward with his/her hand that is gripping the operating part 204 of the treatment tool 200, the slider body 402 does not move with respect to the outer tube 300 (long tubular outer tube body 320), but only the sleeve 440 moves forward with respect to the slider body 402 within the movable range thereof with respect to the slider body 402. For that reason, with respect to the forward movement of the treatment tool insertion part 202 until the sleeve 440 reaches the front end of the movable range thereof with respect to the slider body 402, as illustrated in (B) part of FIG. 13, only the treatment tool insertion part 202 moves forward in a state where the endoscope insertion part 102 is stationary. That is, the slider 400 has the non-sensing region where the endoscope insertion part 102 does not interlock with the forward and backward movement of the treatment tool insertion part 202, and the forward movement operation of the treatment tool 200 at this time becomes a forward and backward movement operation of the slider 400 in the non-sensing region.

Similarly, supposing the state of (A) part of FIG. 13 is a state where the sleeve 440 reaches neither the front end nor the rear end of the movable range thereof with respect to of the slider body 402 (guide part 460) as illustrated in FIG. 10, and if the operator minutely moves the treatment tool insertion part 202 backward with his/her hand that is gripping the operating part 204 of the treatment tool 200, the slider body 402 does not move with respect to the outer tube 300 (long tubular outer tube body 320), but only the sleeve 440 moves backward with respect to the slider body 402 within the movable range thereof with respect to the slider body 402. For that reason, with respect to the backward movement of the treatment tool insertion part 202 until the sleeve 440 reaches the rear end of the movable range thereof with respect to the slider body 402, as illustrated in (C) part of FIG. 13, only the treatment tool insertion part 202 moves backward in a state where the endoscope insertion part 102 is stationary. That is, the backward movement operation of the treatment tool 200 at this time becomes a backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation image to be displayed on the monitor 112 does not vary, and the size of a target to be observed can be prevented from fluctuating according to minute displacement of the treatment tool 200. Accordingly, a sense of perspective can be suitably maintained, and a stable observation image can be provided.

Figure 11:
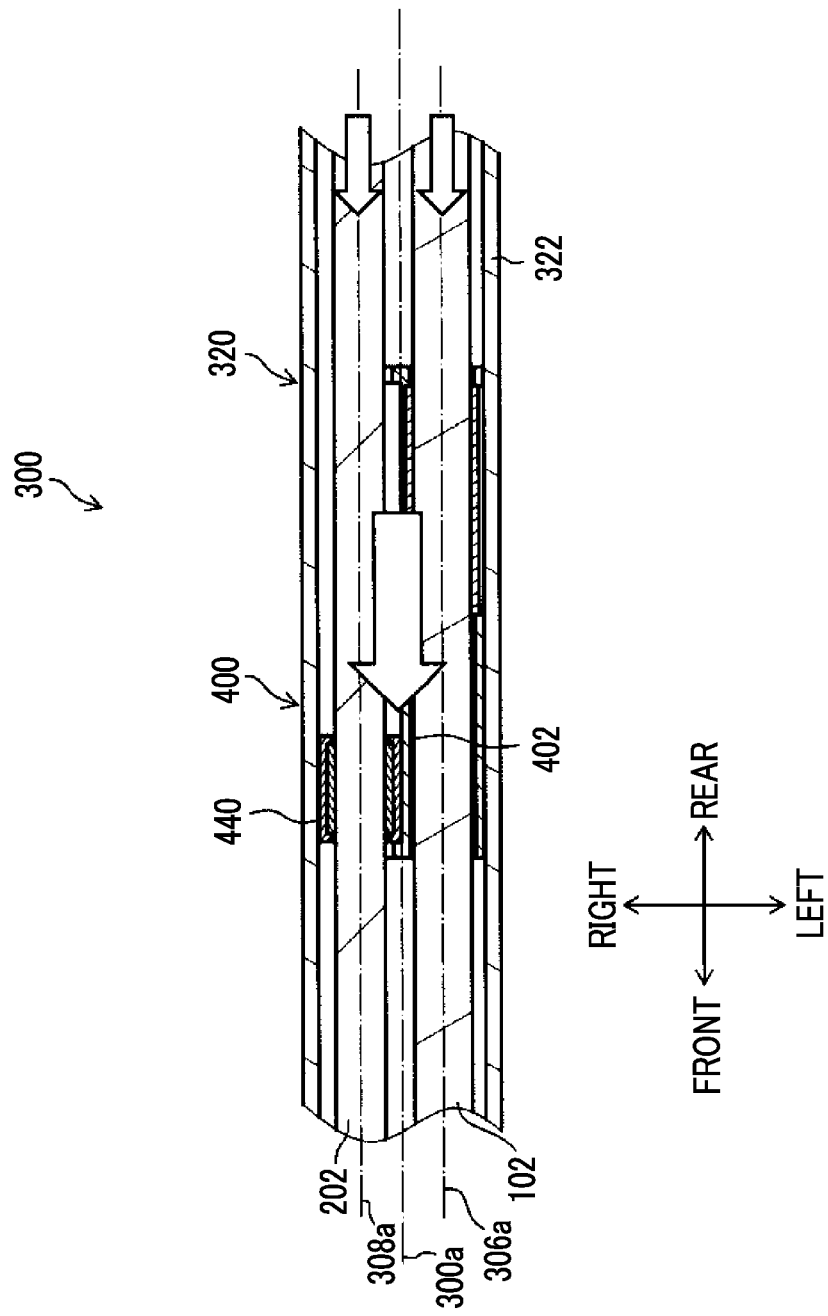
FIG. 11 is an explanatory view used for the description of the working of the slider (interlocking member).

Meanwhile, if the operator greatly moves the treatment tool insertion part 202 forward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the front end of the movable range thereof with respect to the slider body 402 as illustrated in FIG. 11 is brought into after the forward movement of the sleeve 440 of the slider 400 in the non-sensing region until it abuts against the front end of the movable range. Then, if the treatment tool insertion part 202 further moves forward, the sleeve 440 and the slider body 402 moves forward with respect to the long tubular outer tube body 320 together with the treatment tool insertion part 202. As a result, the endoscope insertion part 102 moves forward in an interlocking manner with the treatment tool insertion part 202. For that reason, with respect to the forward movement of the treatment tool insertion part 202 after the sleeve 440 reaches the front end of the movable range thereof with respect to the slider body 402, the endoscope insertion part 102 moves forward in an interlocking manner with the treatment tool insertion part 202 as illustrated in (B) part of FIG. 14, compared to the state of (A) part of FIG. 14 illustrating the same state as (A) part of FIG. 13. That is, the slider 400 has the sensing region where the endoscope insertion part 102 interlocks with the forward and backward movement of the treatment tool insertion part 202, and the forward movement operation of the treatment tool 200 at this time becomes a forward movement operation of the slider 400 in the sensing region.

Figure 12:
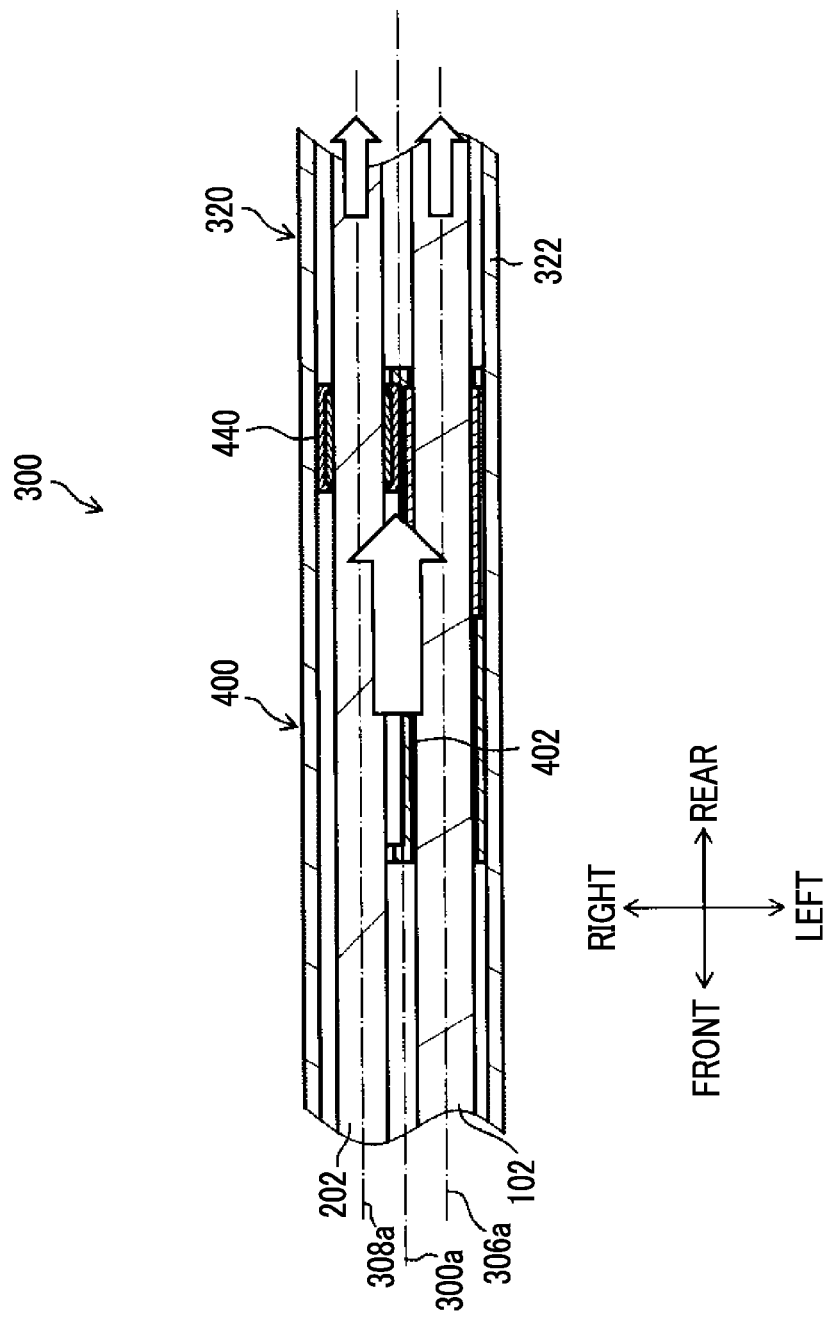
FIG. 12 is an explanatory view used for the description of the working of the slider (interlocking member).

Similarly, if the operator greatly moves the treatment tool insertion part 202 backward with his/her hand that is gripping the operating part 204 of the treatment tool 200 in a state where the sleeve 440 reaches neither the front end nor the rear end of the movable range thereof with respect the slider body 402 as illustrated in FIG. 10, a state where the sleeve 440 reaches the rear end of the movable range thereof with respect to the slider body 402 as illustrated in FIG. 12 is brought into after the backward movement of the sleeve 440 of the slider 400 in the non-sensing region until it abuts against the rear end of the movable range. Then, if the treatment tool insertion part 202 further moves backward, the sleeve 440 and the slider body 402 moves backward with respect to the long tubular outer tube body 320 together with the treatment tool insertion part 202. As a result, the endoscope insertion part 102 moves backward in an interlocking manner with the treatment tool insertion part 202. For that reason, with respect to the backward movement of the treatment tool insertion part 202 after the sleeve 440 reaches the rear end of the movable range thereof with respect to the slider body 402, as illustrated in (C) part of FIG. 14, the endoscope insertion part 102 moves backward in an interlocking manner with the treatment tool insertion part 202. That is, the backward movement operation of the treatment tool 200 at this time becomes a backward movement operation of the slider 400 in the sensing region.

Hence, since the endoscope 100 moves forward and backward with respect to a large forward and backward movement operation of the treatment tool 200, that is, the forward and backward movement operation thereof in the sensing region, the range of an observation image to be displayed on the monitor 112 is continuously changed so as to follow the forward and backward movement of the treatment tool 200. Accordingly, since the size of a target to be observed varies according to the operation of the treatment tool 200, the operator can simply obtain a desired image.

As described above, in a case where the displacement of the treatment tool insertion part 202 in the axial direction is large (in a case where a large amplitude of forward and backward movement has been performed) when an operator has moved the treatment tool insertion part 202 forward and backward in the axial direction, the endoscope insertion part 102 also moves in an interlocking manner forward, backward, up, down, right, and left. Thus, the visual field, orientation, and the like of the endoscope 100 can be changed as intended by an operator. Additionally, the visual field is always given to pick up an image of the distal end of the treatment tool, and consequently, an image that is optimal for treatment is automatically provided. In a case where it is desired to check sites other than a site to be treated, the checking can be performed by moving the treatment tool insertion part 202, and an operator can perform operations as desired. Hence, an assistant (endoscopic technician) who operates the endoscope 100 apart from the operator can be made unnecessary, and a troublesome condition in which the operator should instruct an assistant about the visual field, orientation, and the like of the endoscope 100 serially can be eliminated.

Additionally, in a case where the displacement of the treatment tool insertion part 202 in the axial direction is small (in a case where a small amplitude of forward and backward movement has been performed), the endoscope insertion part 102 does not interlock. Therefore, the size of a target to be observed within an observation image can be prevented from fluctuating unnecessarily, a sense of perspective can be suitably maintained, and a stable observation image can be provided.

Figure 15:
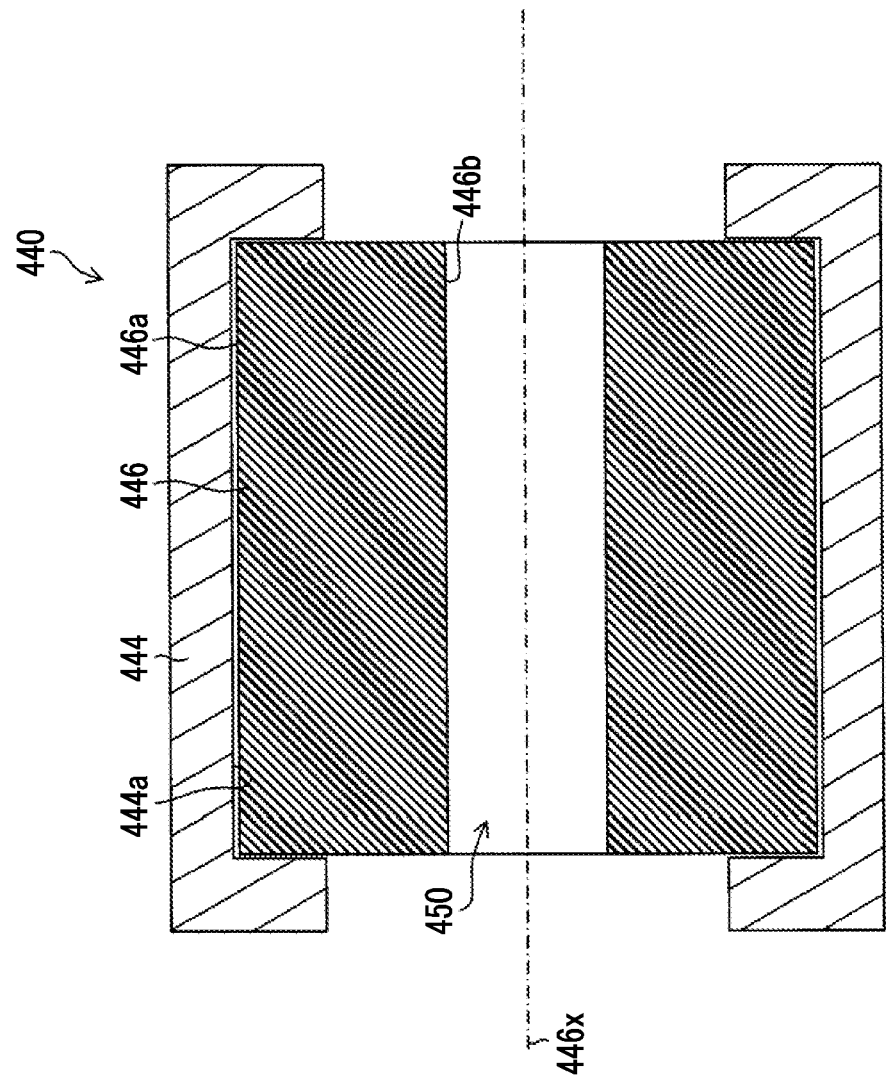
FIG. 15 is a cross sectional view when a sleeve is cut in a plane along an axis.

Next, the pressure-contact member 446 fixed inside the sleeve 440 of the slider 400 as illustrated in FIG. 7 and the like will be described. FIG. 15 is a cross sectional view when the sleeve 440 is cut in a plane along an axis 446x (treatment tool insertion axis 308a) passing through the center of the sleeve.

As illustrated in FIGS. 7 and 15, the sleeve 440 consists of a hard sleeve body 444 and the pressure-contact member 446 serving as the fixed member fixed inside the sleeve body 444, and the pressure-contact member 446 is formed in a cylindrical shape using foamed rubber as one form of a foamed elastic body having a number of pores.

The treatment tool insertion part 202 inserted through the treatment tool insertion passage 308 of the outer tube 300 as described above is inserted through the through-hole 450 of the pressure-contact member 446, and the pressure-contact member 446 is brought into pressure contact with (frictionally engaged with) the entire outer peripheral surface of the treatment tool insertion part 202 in its circumferential direction. Accordingly, the treatment tool insertion part 202 is coupled to the sleeve 440 via the pressure-contact member 446 and is coupled to the treatment tool-coupling part 422 of the slider 400.

In the surgical apparatus for an endoscope 10 of the present embodiment, the treatment tool 200 that is not limited to specific types (applications, manufacturers, and the like), and the external diameter of the treatment tool insertion part 202 varies depending on the types of treatment tools 200 to be used. For example, although surgical forceps generally called 5 mm forceps are used, the external diameter of the 5 mm forceps is not unified, and 5 mm forceps with an external diameter of 4 mm to 6 mm is present.

Meanwhile, it is necessary to make the diameter of the through-hole 450 of the pressure-contact member 446 smaller than the external diameter of the treatment tool insertion part 202 in order to bring the pressure-contact member into pressure contact with the outer peripheral surface of the treatment tool insertion part 202. Hence, the diameter of the through-hole 450 is smaller than at least the external diameter of a treatment tool of which the external diameter of the treatment tool insertion part is the smallest, among treatment tools available in the surgical apparatus for an endoscope 10.

Figure 16:
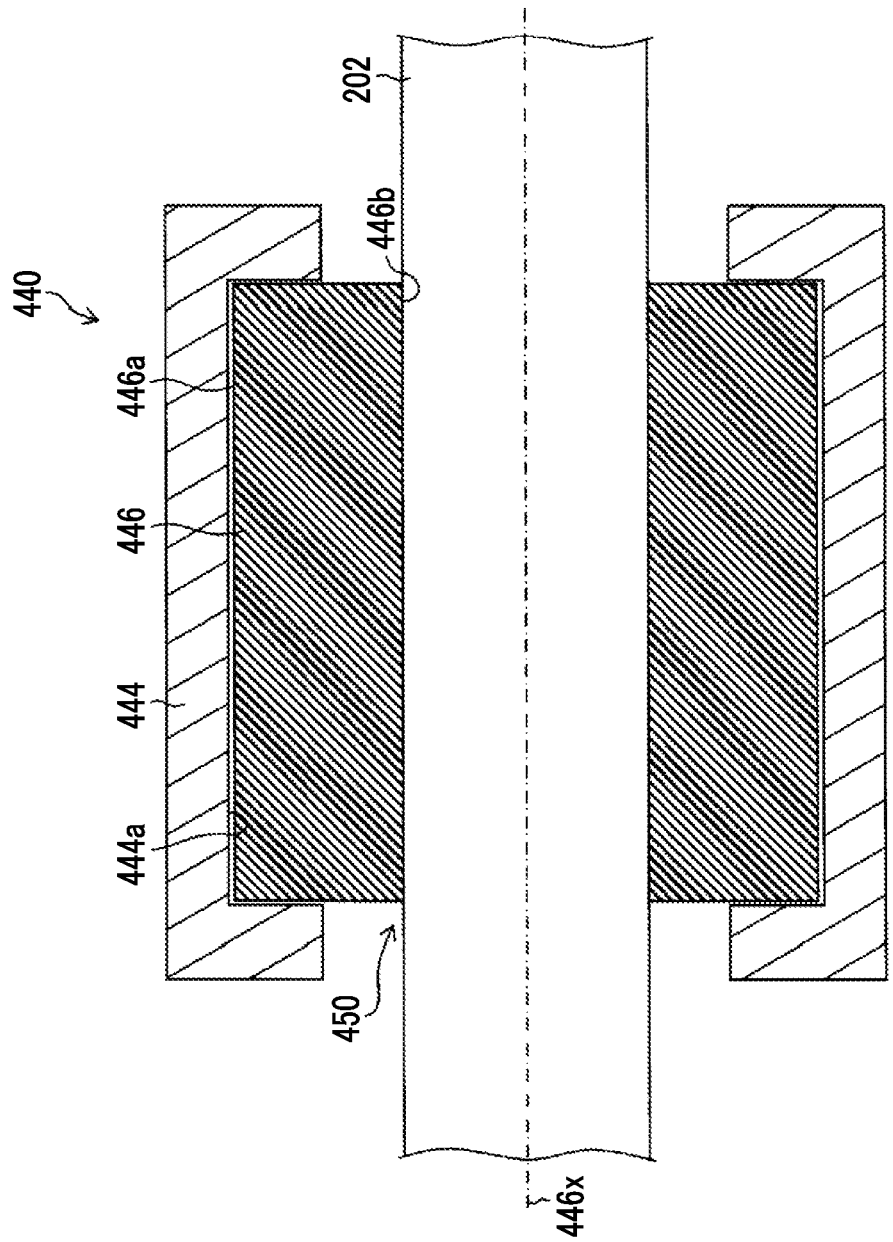
FIG. 16 is a cross sectional view illustrating a state where a treatment tool insertion part is inserted through the sleeve.

Accordingly, if the treatment tool insertion part 202 of an available arbitrary treatment tool 200 is inserted through the through-hole 450 of the pressure-contact member 446, as illustrated in FIG. 16, the through-hole 450 of the pressure-contact member 446 is enlarged in diameter to a size such that the treatment tool insertion part 202 is insertable therethrough. In this case, an inner peripheral surface (a peripheral surface of the through-hole 450) of the pressure-contact member 446 is brought into pressure contact with the outer peripheral surface of the treatment tool insertion part 202 by a restoring force of the pressure-contact member 446 to its original shape. Unless a force equal to or more than a certain value in a direction of the axis 446x or a direction around the axis 446x is applied between the pressure-contact member 446 and the treatment tool insertion part 202, the treatment tool insertion part 202 is fixed in a state where the treatment tool insertion part does not move in the direction of the axis 446x and in the direction around the axis 446x with respect to the pressure-contact member 446 by a frictional force therebetween.

Figure 17:
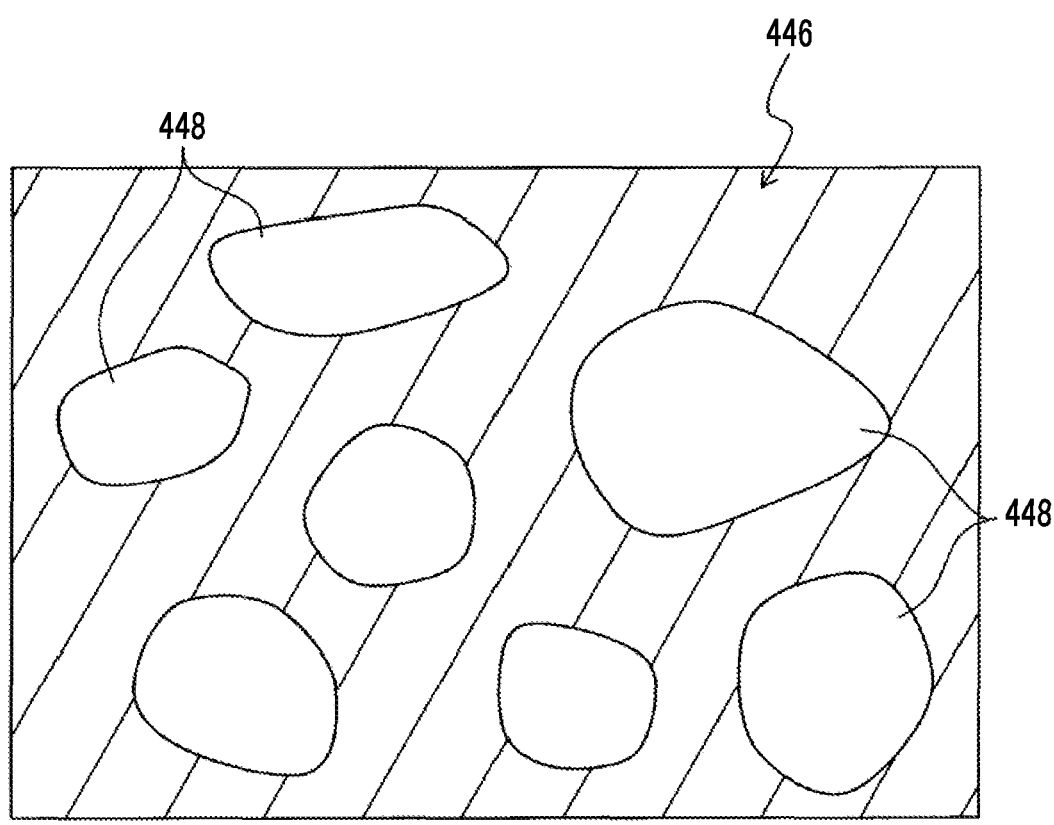
FIG. 17 is an enlarged cross sectional view schematically illustrating pores inside a pressure-contact member (foamed rubber).

Additionally, the pressure-contact member 446 is formed of the foamed rubber as described above. The foamed rubber has a number of pores 448, which are a number of pores, therein as illustrated in the enlarged cross sectional view of FIG. 17. As specific materials of the foamed rubber, the following ones in which a 25% compressive load is equal to or more than 35 (kPa) and equal to or less than 170 (kPa) are suitable.

Urethane
EPDM (ethylene propylene diene rubber)
Natural rubber
NBR (nitrile rubber)
Fluororubber
CR (chloroprene rubber) (polychloroprene)
Silicone rubber In addition, as the foamed rubber that forms the pressure-contact member 446, foamed rubber with closed pores in which the pores 448 are not connected together may be used, or foamed rubber in which open pores (continuous pores) in which the pores 448 are connected together may be used.

Additionally, the pressure-contact member 446 may be formed of foamed elastic bodies other than the foamed rubber of the above materials.

Since the pressure-contact member 446 formed of such foamed rubber is contractable, there are the following advantages as compared to a case where the pressure-contact member 446 is formed of a solid elastic body in which contraction hardly occurs.

First, even in a case where an outer peripheral surface 446a of the pressure-contact member 446 is made to contact or approach an inner peripheral surface 444a of the sleeve body 444 and is fixed as illustrated in FIG. 15, the treatment tool insertion part 202 with a large external diameter is insertable.

For example, in the case where the pressure-contact member 446 is formed of the solid elastic body, the volume thereof is held even if the pressure-contact member is deformed. For that reason, when the treatment tool insertion part 202 with a larger external diameter than the diameter of the through-hole 450 is inserted through the through-hole 450, the pressure-contact member 446 is going to increase in its radial direction as much as the through-hole 450 is enlarged in diameter.

However, in a case where the outer peripheral surface 446a of the pressure-contact member 446 is made to contact or approach the inner peripheral surface 444a of the sleeve body 444 as in the present embodiment, at least the enlargement of the pressure-contact member 446 in the radial direction is restricted, and only the enlargement of the pressure-contact member 446 in the direction of the axis 446*x* is allowed. For this reason, a large force is required for the enlargement of the diameter of the through-hole 450, and the external diameter of the treatment tool insertion part 202 that is insertable through the through-hole 450 of the pressure-contact member 446 becomes smaller than that in a case where the pressure-contact member 446 is made of the foamed rubber.

In other words, in the pressure-contact member 446 in which the variation of the external diameter is restricted, if a case where the pressure-contact member 446 is formed of the foamed rubber is compared with the case where the pressure-contact member is formed of the solid elastic body, the treatment tool insertion part 202 with a larger external diameter is insertable in the case where the pressure-contact member 446 is formed of the foamed rubber if the diameter of the through-hole 450 is the same. Additionally, if of the treatment tool insertion part 202 with the same external diameter is made insertable, the minimum diameter of the through-hole 450 can be made smaller in the case where the pressure-contact member 446 is formed of the foamed rubber.

Hence, by forming the pressure-contact member 446 of the foamed rubber to make the diameter of the through-hole 450 small, the external diameter of the pressure-contact member 446 can be made small, and the external diameter of the sleeve body 444 can be made small. Accordingly, the external diameter of the sleeve 440 can be made small, and the diameter of the outer tube 300 (long tubular outer tube body 320) can be reduced. Additionally, by making the diameter of the through-hole 450 small, the minimum external diameter of the treatment tool insertion part 202 that is engageable with the pressure-contact member 446 becomes small. Therefore, the range of the external diameter of the treatment tool insertion part 202 that is engageable with the pressure-contact member 446 can also be expanded.

Additionally, in the case where the pressure-contact member 446 is formed of the solid elastic body, it is possible to provide a gap between the outer peripheral surface 446*a* of the pressure-contact member 446 and the inner peripheral surface 444*a* of the sleeve body 444 to enlarge the external diameter of the treatment tool insertion part 202 that is insertable through the through-hole 450. However, the external diameter of the sleeve 440 becomes larger as much as the gap is provided. Additionally, If the gap is provided, in the case where the pressure-contact member 446 is formed of the foamed rubber, the diameter of the through-hole 450 and the external diameter of the pressure-contact member 446 can be made small, and the external diameter of a sleeve 440 can be made smaller than that in a case where no gap is provided. Hence, by forming the pressure-contact member 446 by foamed rubber even in the sleeve 440 having a form in which the gap is provided between the outer peripheral surface 446*a* of the pressure-contact member 446 and the inner peripheral surface 444*a* of the sleeve body 444 unlike the present embodiment, the diameter of the outer tube 300 (long tubular outer tube body 320) can be reduced, and the range of the external diameter of the treatment tool insertion part 202 that is engageable with the pressure-contact member 446 can also be expanded.

From the above, limitation of the type of treatment tool 200 available in the surgical apparatus for an endoscope 10 of the present embodiment is eased, and convenience is improved.

Moreover, in the case where the pressure-contact member 446 is formed of the foamed rubber as in the present embodiment, the pores 448 in a region along at least an inner peripheral surface 446*b* (a peripheral surface of the through-hole 450) of the pressure-contact member 446 can be made to hold an oil component.

For example, an oil component or the like in a living body may adhere to the inner peripheral surface 446*b* of the pressure-contact member 446 during treatment. In that case, since the frictional force between the inner peripheral surface 446*b* of the pressure-contact member 446 and the outer peripheral surface of the treatment tool insertion part 202 varies, a holding force of the treatment tool insertion part 202 by the pressure-contact member 446 fluctuates.

If the fluctuation of this holding force occurs, the treatment tool insertion part 202 moves with respect to the pressure-contact member 446 (an engagement position between the sleeve 440 and the treatment tool insertion part 202 deviates) irrespective of an operator's unintended action. On the other hand, if an initial holding force is set such that a sufficient holding force is maintained even if an oil component adheres, a situation in which the treatment tool insertion part 202 does not move with respect to the pressure-contact member 446 may occur irrespective of the operator's intention, for example, immediately after the beginning of use.

Such a situation can be prevented by making the pores 448 of the pressure-contact member 446 hold an oil component in advance.

Namely, even in a case where adhesion of an oil component or the like from the outside has occurred in the pressure-contact member 446, a significant fluctuation does not occur in the frictional force between the inner peripheral surface 446*b* of the pressure-contact member 446 and the outer peripheral surface of the treatment tool insertion part 202 by virtue of the oil component made to be held in advance by the pores 448 of the pressure-contact member 446, and the holding force of the treatment tool insertion part 202 by the pressure-contact member 446 can be maintained at a certain holding force that is assumed in advance at the time of design or the like. Accordingly, operability is improved regarding the operation of the treatment tool 200.

In addition, the pores 448 of the entire pressure-contact member 446 may be made to hold an oil component, and only the pores 448 of the region along the inner peripheral surface of the pressure-contact member 446 (the peripheral surface of the through-hole 450) may be made to hold the oil component as described above.

Additionally, in a case where the foamed rubber that forms the pressure-contact member 446 is the above-described closed pores, fine recesses caused by the pores 448 are formed in the surface of the inner peripheral surface of the pressure-contact member. Therefore, the recesses can be made to hold an oil component. In the case where the foamed rubber that forms the pressure-contact member 446 is the above-described open pores, the pores 448 inside the pressure-contact member 446 can be made to hold an oil component. Therefore, the oil component can be maintained even if the pressure-contact member is used for a long time.

However, it is possible to select whether or not the foamed rubber that forms the pressure-contact member 446 is made to hold an oil component, and the pressure-contact member 446 may not hold the oil component.

Figure 18:
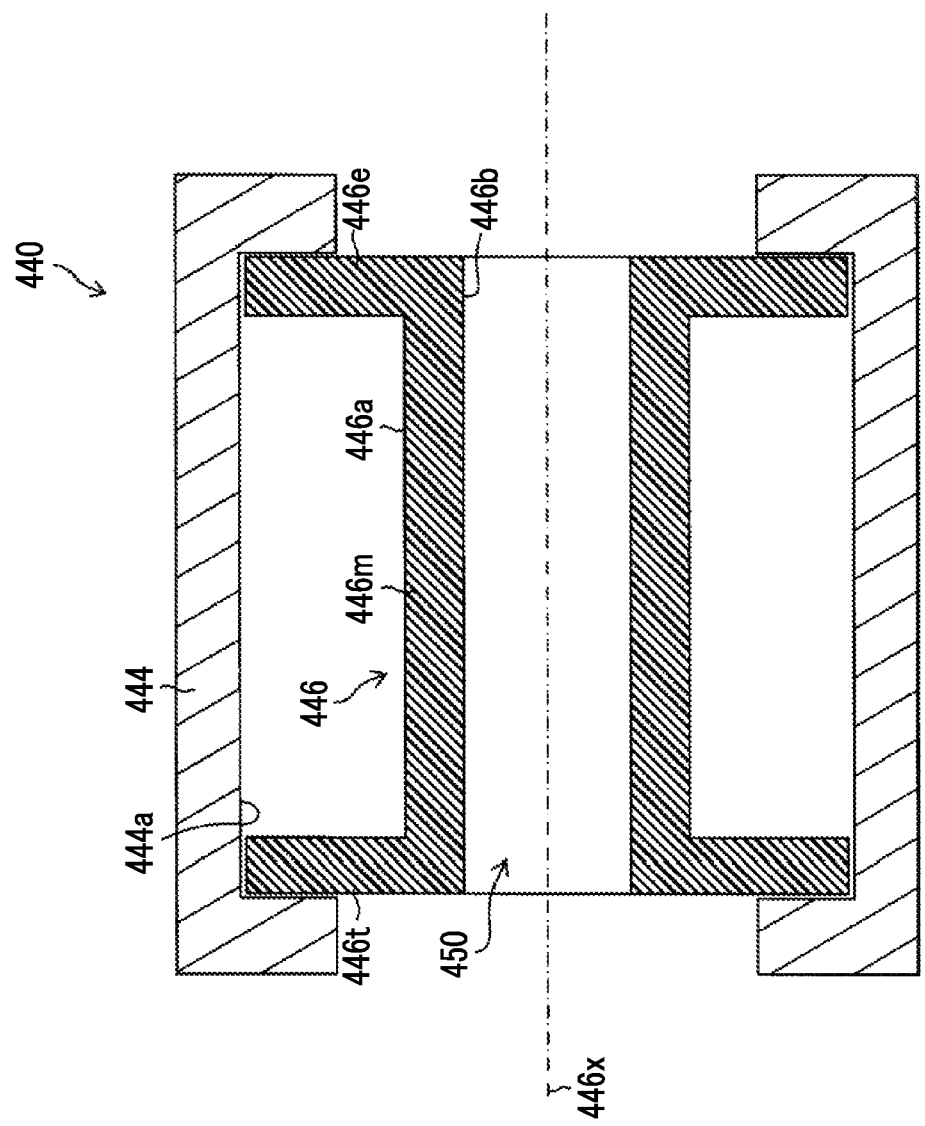
FIG. 18 is a cross sectional view of a sleeve illustrating another embodiment of the pressure-contact member.

Next, another embodiment of the pressure-contact member 446 will be described. FIG. 18 is a cross sectional view when the sleeve 440 including the pressure-contact member 446 of the other embodiment is cut in a plane along the axis 446x (treatment tool insertion axis 308a), constituent elements having functions same as or similar to those of FIGS. 7 and 15 will be designated by the same reference signs, and the description thereof will be omitted.

The pressure-contact member 446 in this drawing is formed in a cylindrical shape using the foamed rubber, similar to the above embodiment. The pressure-contact member 446 has a smaller-diameter part 446m configured to have a smaller external diameter than a distal end part 446t and a base end part 446e between the distal end part 446t on the distal end side that is one end part in the direction of the axis 446x and the base end part 446e on the base end side that is the other end part.

Namely, the distal end part 446t and the base end part 446e have a larger external diameter than the smaller-diameter part 446m, and openings of the through-hole 450 through which the treatment tool insertion part 202 is inserted are formed in an end surface on the distal end side of the distal end part 446t and an end surface of the base end part 446e on the base end side that become end surfaces of the pressure-contact member 446 on the distal end side and the base end side.

In addition, only the openings of the through-hole 450 are provided in the end surface of the distal end part 446t on the distal end side and the end surface of the base end part 446e on the base end side, and a hole such that the treatment part 206 of the distal end of the treatment tool 200 is caught therein is not present.

According to this, in the smaller-diameter part 446m of which the outer shape is made small, a space is formed between the outer peripheral surface 446a and the inner peripheral surface 444a of the sleeve body 444. When the treatment tool insertion part 202 is inserted through the through-hole 450 of the pressure-contact member 446, by virtue of the space the pressure-contact member 446 is not only easily deformed by contraction but also easily deformed by causes other than the contraction.

Hence, in the pressure-contact member 446 of the present embodiment, the amount of deformation can be enlarged as compared with a case where deformation of only contraction occurs substantially like the pressure-contact member 446 illustrated in FIG. 15, and a large amount of deformation can be secured while minimizing fluctuation of the holding force, though volume is small. From this, the size and the diameter of the pressure-contact member 446 and the sleeve 440 can be reduced, and the diameter of the outer tube 300 (long tubular outer tube body 320) can be reduced.

In addition, also in the pressure-contact member 446 of the present embodiment, the pores 448 of the pressure-contact member 446 can be made to hold an oil component as described above.

Figure 19:
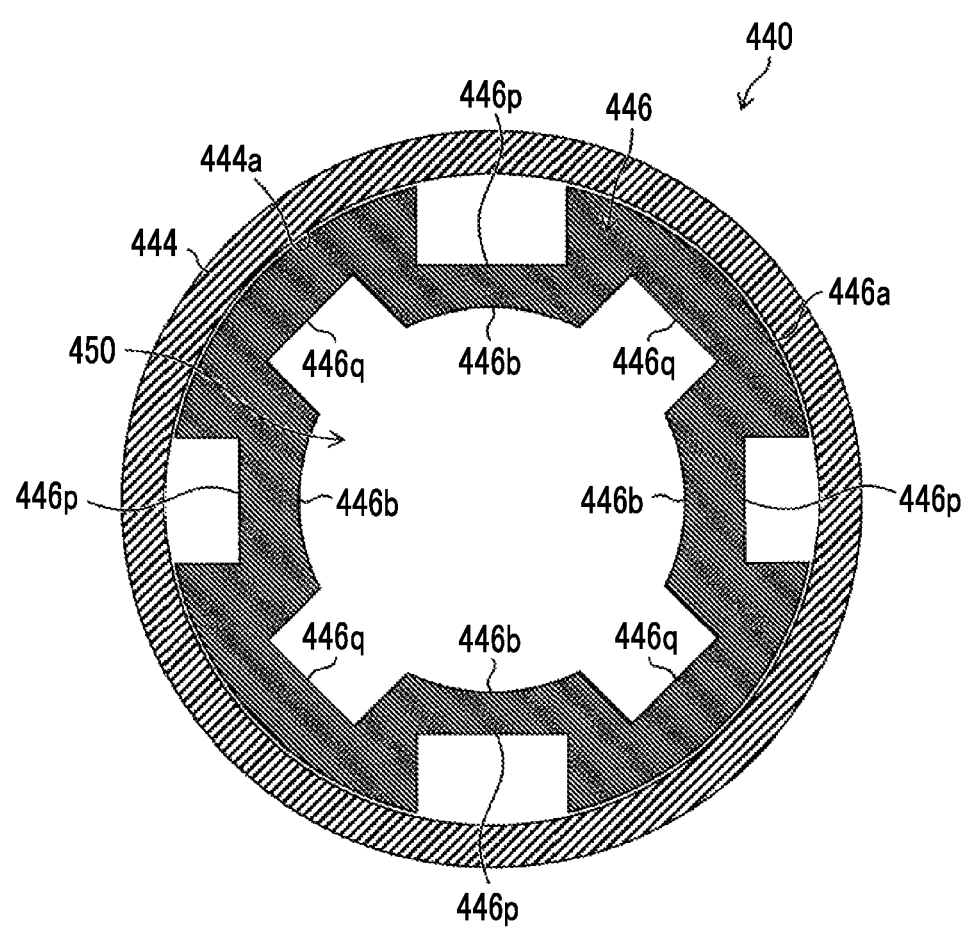
FIG. 19 is a cross sectional view of a sleeve illustrating still another embodiment of the pressure-contact member.

Additionally, similar to the embodiment of FIG. 18, deformation other than contraction can also be made possible by providing a space in the pressure-contact member 446 as in an embodiment illustrated in FIG. 19. FIG. 19 is a cross sectional view when the sleeve 440 is cut in a plane orthogonal to the axis 446x. The pressure-contact member 446 illustrated in this drawing has four grooves 446p along the axis 446x on an outer peripheral surface 446a side, and four grooves 446q along the axis 446x on an inner peripheral surface 446b side. Accordingly, a plurality of spaces are provided on the outer peripheral surface 446a side and the inner peripheral surface 446b side of the pressure-contact member 446. However, when an end of the pressure-contact member 446 is seen from the direction of the axis 446x, openings other than through-hole 450 are present. For that reason, when the treatment tool 200 is inserted through the through-hole 450, the treatment part 206 of the distal end of the treatment tool 200 may be caught in the openings other than through-hole 450, or the treatment tool 200 may be not easily inserted through the through-hole 450.

Hence, at least on the base end side of the pressure-contact member 446, it is desirable not to provide holes other than the openings of the through-hole 450 unlike the embodiment of FIG. 18.

The pressure-contact member 446 coupled to the treatment tool insertion part 202 inserted through the treatment tool insertion passage 308 of the outer tube 300 has been described above. However, the same configuration as the above embodiment regarding the pressure-contact member 446 can be adopted in not only the pressure-contact member 446 but also the pressure-contact member 426 that is the fixed member illustrated in FIGS. 7 and 8 coupled to the endoscope insertion part 102 inserted through the endoscope insertion passage 306 of the outer tube 300. Additionally, the pressure-contact member 426 can also be formed of the foamed rubber. Additionally, the pores of a region along at least an inner peripheral surface of the pressure-contact member 426 can also be made to hold an oil component.

In the case of the endoscope 100, since there is less necessity for using different types of endoscopes than the treatment tool 200, available endoscopes 100 can also be limited to those in which the endoscope insertion part 102 has specific external diameters. However, even in that case, by forming the pressure-contact member 426 using the foamed rubber, the diameter of the pressure-contact member 426 can be reduced, which can contribute to reduction in the diameter of the outer tube 300 (long tubular outer tube body 320). Additionally, endoscopes 100 in which the external diameters of the endoscope insertion part 102 are different from each other like the treatment tool 200 can also be made usable, an convenience can be improved. Moreover, operability can also be improved by making the pores (the pores of the foamed rubber) of the pressure-contact member 426 hold an oil component.

In addition, the pressure-contact member 426 or the pressure-contact member 446 of the foamed rubber in which at least one coupling part of the endoscope-coupling part 420 or the treatment tool-coupling part 422 is made to hold an oil component as in the above embodiment may be adopted, and one coupling part of the endoscope-coupling part 420 or the treatment tool-coupling part 422 may be different from that of the above embodiment.

As described above, although the surgical apparatus for an endoscope 10 of the above embodiment include the outer tube 300 that guides the endoscope insertion part 102 of the endoscope 100 and the treatment tool insertion part 202 of the treatment tool 200 into a body cavity, the invention is not limited to this, and can be applied to a surgical apparatus for an endoscope including an outer tube that guides two arbitrary medical instruments into a body cavity, and the outer tube.

That is, the invention includes a surgical apparatus for an endoscope and an outer tube having the following configuration.

The surgical apparatus for an endoscope includes a first medical instrument having a first insertion part to be inserted into a body cavity, a second medical instrument having a second insertion part to be inserted into the body cavity, and an outer tube that passes through a body wall, is inserted into the body cavity, and guides the first insertion part and the second insertion part into the body cavity. The endoscopes 100 and the endoscope insertion part 102 in the above embodiment are one form of the first medical instrument and the first insertion part, and the treatment tool 200 and the treatment tool insertion part 202 are one form of the second medical instrument and the second insertion part.

The outer tube includes an outer tube body having a distal end, a base end, and a longitudinal axis, a first distal end opening and a second distal end opening equivalent to the above-described first distal end opening 312 and the second distal end opening 316 that are provided at a distal end of the outer tube body, a first base end opening and a second base end opening equivalent to the above-described first base end opening 310 and the second base end opening 314 that are provided at a base end of the outer tube body, a first insertion passage equivalent to the above-described endoscope insertion passage 306 that is provided along the longitudinal axis of the outer tube body, allows the first distal end opening and the first base end opening to communicate with each other, and has the first insertion part to be inserted therethrough so as to be movable forward and backward, a second insertion passage equivalent to the above-described treatment tool insertion passage 308 that is provided along the longitudinal axis of the outer tube body, allows the second distal end opening and the second base end opening to communicate with each other, and has the second insertion part to be inserted therethrough so as to be movable forward and backward, an interlocking member equivalent to the above-described slider 400 that has a first coupling part equivalent to the above-described endoscope-coupling part 420 to be coupled to the first insertion part inserted through the first insertion passage and a second coupling part equivalent to the above-described treatment tool-coupling part 422 to be coupled to the second insertion part inserted through the second insertion passage, and moves inside the outer tube body so as to be movable forward and backward, and a fixed member equivalent to the above-described pressure-contact member 426 or the above-described pressure-contact member 446 that is provided in at least one coupling part of the first coupling part or the second coupling part, has an inner peripheral surface contacting an entire outer peripheral surface, in a circumferential direction, of an insertion part to be coupled to the coupling part, is made of a foamed elastic body, such as foamed rubber that has a number of pores, and makes the pores hold an oil component.

EXPLANATION OF REFERENCES

10: surgical apparatus for endoscope
100: endoscope
102: endoscope insertion part
104: cable part
108: processor device
110: light source device
112: monitor
116: observation window
118: illumination window
130: forward and backward movement operating part
200: treatment tool
202: treatment tool insertion part
204: operating part
206: treatment part
300: outer tube
300a: reference axis
302: base end surface
306: endoscope insertion passage
306a: endoscope insertion axis
308: treatment tool insertion passage
308a: treatment tool insertion axis
310: first base end opening
312: first distal end opening
314: second base end opening
316: second distal end opening
320: long tubular outer tube body
340: base end cap
360: distal end cap
400: slider
402: slider body
420: endoscope-coupling part
422: treatment tool-coupling part
426, 446: pressure-contact member
440: sleeve
444: sleeve body
446a: outer peripheral surface
446e: base end part
446m: smaller-diameter part
446t: distal end part
446x: shaft
448: pore
460: guide part
462: guide surface
466, 468: end edge part
500: exterior tube

What is claimed is:

1. A surgical apparatus for an endoscope comprising:
a first medical instrument having a first insertion part configured to be inserted into a body cavity;
a second medical instrument having a second insertion part configured to be inserted into the body cavity; and
an outer tube that is configured to be passed through a body wall, to be inserted into the body cavity, and to guide the first insertion part and the second insertion part into the body cavity,
wherein the outer tube includes
an outer tube body having a distal end, a base end, and a longitudinal axis,
a first distal end opening and a second distal end opening provided at the distal end of the outer tube body,
a first base end opening and a second base end opening provided at the base end of the outer tube body,
a first insertion passage that is provided along the longitudinal axis of the outer tube body, communicates between the first distal end opening and the first base end opening, and where the first insertion part is inserted therethrough so as to be movable forward and backward,
a second insertion passage that is provided along the longitudinal axis of the outer tube body, communicates between the second distal end opening and the second base end opening, and where the second insertion part inserted therethrough so as to be movable forward and backward,
an interlocking member that has a first coupling part to be coupled to the first insertion part inserted through the first insertion passage and a second coupling part to be coupled to the second insertion part inserted through the second insertion passage, and is movable forward and backward inside the outer tube body,
wherein each of the first coupling part and the second coupling part comprises:
a respective fixed member having an inner peripheral surface contacting an outer peripheral surface, in a circumferential direction, of the first insertion part or the second insertion part to be coupled to the first coupling part or the second coupling part, is made of a foamed elastic body having a number of pores, and the pores hold an oil component.

2. The surgical apparatus for an endoscope according to claim 1,
wherein one of the fixed members has a smaller-diameter part formed to have a smaller external diameter than one end part and the other end part thereof in an axial direction between the one end part and the other end part.

3. The surgical apparatus for an endoscope according to claim 1,
wherein the first medical instrument is an endoscope in which an observation part is provided at a distal end of the first insertion part, and
wherein the second medical instrument is a treatment tool in which a treatment part is provided at a distal end of the second insertion part.

4. The surgical apparatus for an endoscope according to claim 3,
wherein one of the fixed members is provided in the second coupling part.

5. The surgical apparatus for an endoscope according to claim 1,
wherein the interlocking member is comprises a sleeve member, and is disposed inside the outer tube body so as to be movable forward and backward, one of the fixed members couples one of the first and second coupling parts to the sleeve member, the sleeve member and the one of the fixed members are fixed to one of the first and second insertion parts and movable with respect to other portions of the interlocking member within a range of the interlocking member, and another one of the fixed members is fixed to another one of the first and second insertion parts as well as other portions of the interlocking member.

6. An outer tube to be used in a surgical apparatus for an endoscope including a first medical instrument having a first insertion part to be inserted into a body cavity, a second medical instrument having a second insertion part to be inserted into the body cavity, and the outer tube configured to be passed through a body wall, is inserted into the body cavity, and to guide the first insertion part and the second insertion part into the body cavity, the outer tube comprising:
an outer tube body having a distal end, a base end, and a longitudinal axis;
a first distal end opening and a second distal end opening provided at the distal end of the outer tube body;
a first base end opening and a second base end opening provided at the base end of the outer tube body;
a first insertion passage that is provided along the longitudinal axis of the outer tube body, communicates between the first distal end opening and the first base end opening, and where the first insertion part is configured to be inserted therethrough so as to be movable forward and backward;
a second insertion passage that is provided along the longitudinal axis of the outer tube body, communicates between the second distal end opening and the second base end opening, and where the second insertion part is configured to be inserted therethrough so as to be movable forward and backward;
an interlocking member that has a first coupling part to be coupled to the first insertion part inserted through the first insertion passage and a second coupling part to be coupled to the second insertion part inserted through the second insertion passage, and is movable forward and backward inside the outer tube body; wherein each of the first coupling part and the second coupling part comprises:
a respective fixed member having an inner peripheral surface contacting an outer peripheral surface, in a circumferential direction, of the first insertion part or the second insertion part to be coupled to the first coupling part or the second coupling part, is made of a foamed elastic body having a number of pores, and the pores hold an oil component.

7. The outer tube according to claim 6,
wherein one of the fixed members has a smaller-diameter part formed to have a smaller external diameter than one end part and the other end part thereof in an axial direction between the one end part and the other end part.

8. The outer tube according to claim 6,
wherein the first medical instrument is an endoscope in which an observation part is provided at a distal end of the first insertion part, and
wherein the second medical instrument is a treatment tool in which a treatment part is provided at a distal end of the second insertion part.

9. The outer tube according to claim 8,
wherein one of the fixed members is provided in the second coupling part.

10. The outer tube according to claim 6,
wherein the interlocking member is comprises a sleeve member, and is disposed inside the outer tube body so as to be movable forward and backward, one of the fixed members couples one of the first and second coupling parts to the sleeve member, the sleeve member and the one of the fixed members are fixed to one of the first and second insertion parts and movable with respect to other portions of the interlocking member within a range of the interlocking member, and another one of the fixed members is fixed to another one of the first and second insertion parts as well as other portions of the interlocking member.

* * * * *